(12) United States Patent
Glaser et al.

(10) Patent No.: US 12,096,961 B2
(45) Date of Patent: Sep. 24, 2024

(54) SURGICAL INSTRUMENT AND METHOD

(71) Applicant: Warsaw Orthopedic, Inc., Warsaw, IN (US)

(72) Inventors: Adam D. Glaser, Collierville, TN (US); Daniel Paxton Wall, Cordova, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 18/074,948

(22) Filed: Dec. 5, 2022

(65) Prior Publication Data

US 2024/0180592 A1 Jun. 6, 2024

(51) Int. Cl.
*A61B 17/70* (2006.01)
*A61B 17/00* (2006.01)

(52) U.S. Cl.
CPC ............ *A61B 17/7013* (2013.01); *A61B 2017/00407* (2013.01); *A61B 2017/00477* (2013.01)

(58) Field of Classification Search
CPC .............. A61B 17/708; A61B 17/7082; A61B 17/7085; A61B 2017/00407; A61B 2017/00477

USPC ......................................... 606/86 A, 99, 104
See application file for complete search history.

(56) References Cited

U.S. PATENT DOCUMENTS

| | | | |
|---|---|---|---|
| 2008/0243133 A1* | 10/2008 | Heinz ................... | B25B 23/101 606/104 |
| 2018/0014862 A1* | 1/2018 | Raina ................... | A61B 17/708 |
| 2022/0370101 A1* | 11/2022 | Italiaie ............... | A61B 17/7082 |

* cited by examiner

*Primary Examiner* — Nicholas J Plionis
*Assistant Examiner* — Christina Negrellirodriguez
(74) *Attorney, Agent, or Firm* — Sorell, Lenna & Schmidt, LLP

(57) ABSTRACT

A surgical instrument is provided that includes a first member defining a longitudinal axis and including a first mating surface engageable with a second mating surface of a fastener. A second member includes an expandable portion. A third member is engageable with the expandable portion to releasably capture the fastener. A first lever is connected to the first member, and a second lever is connected with the first lever via a pivot. The levers being rotatable relative to the longitudinal axis between a non-locked orientation and a locked orientation such that the pivot is rotatable past axial alignment to fix position of the first member relative to the fastener. Systems, spinal constructs, implants and methods are disclosed.

20 Claims, 42 Drawing Sheets

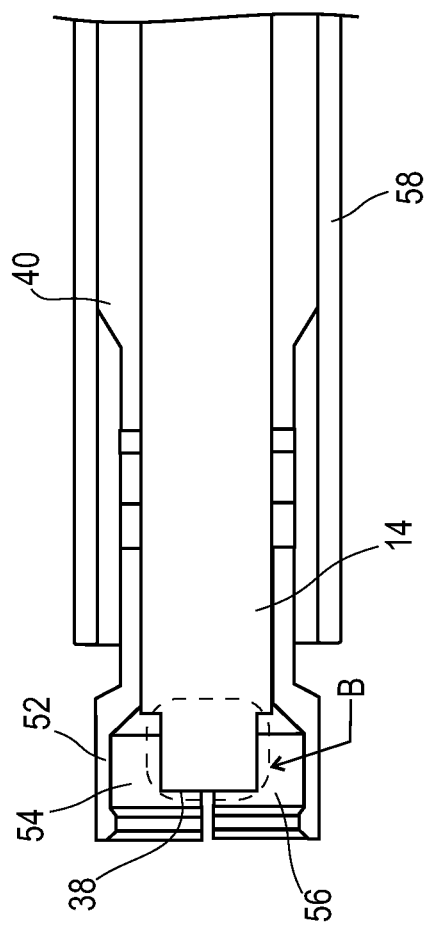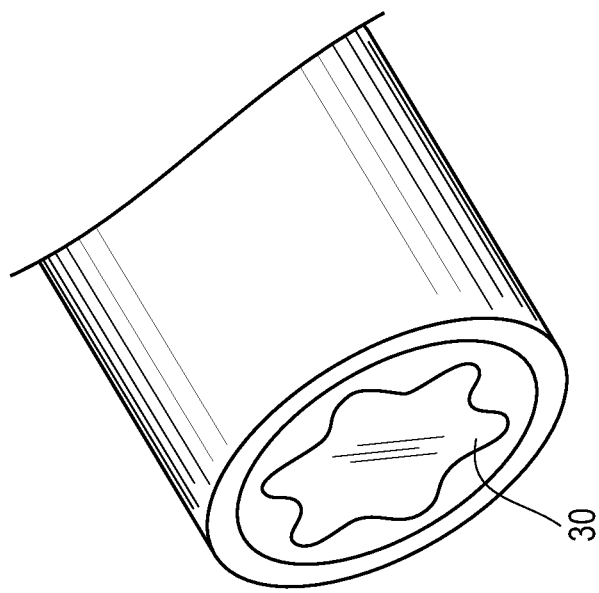

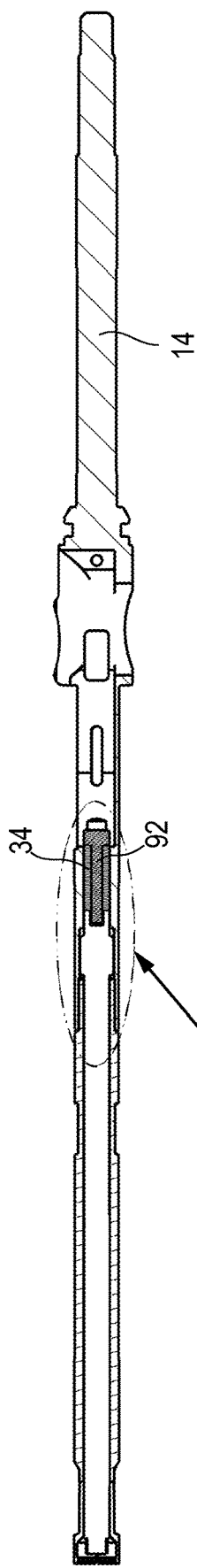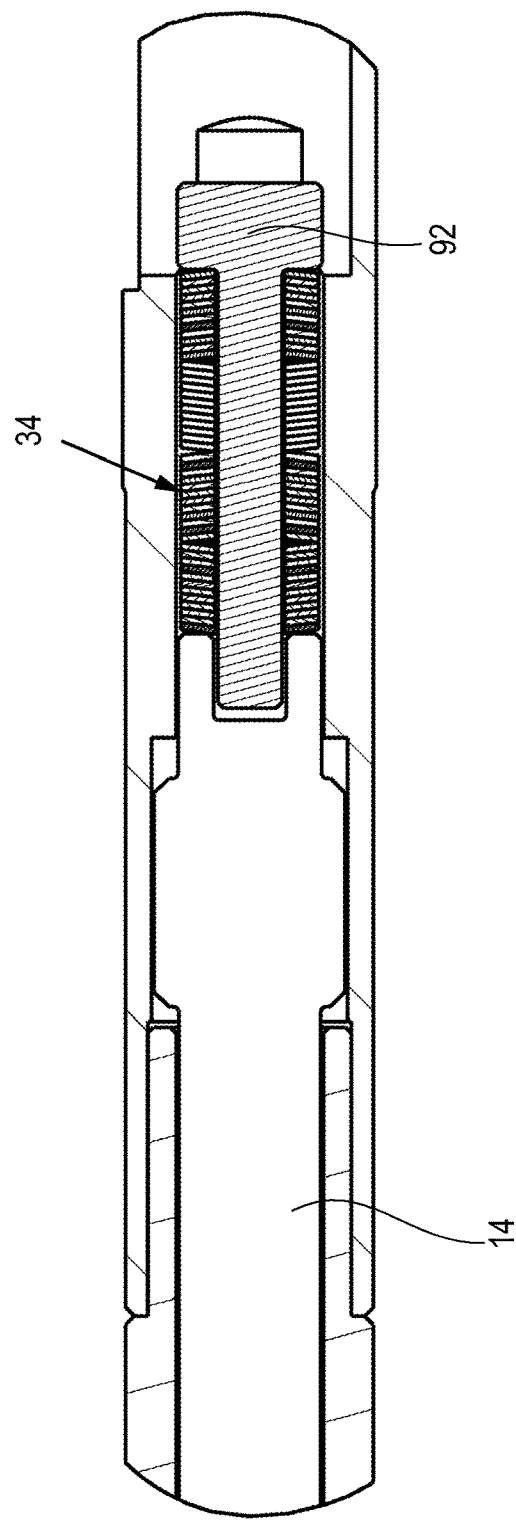
FIG. 9
FIG. 10

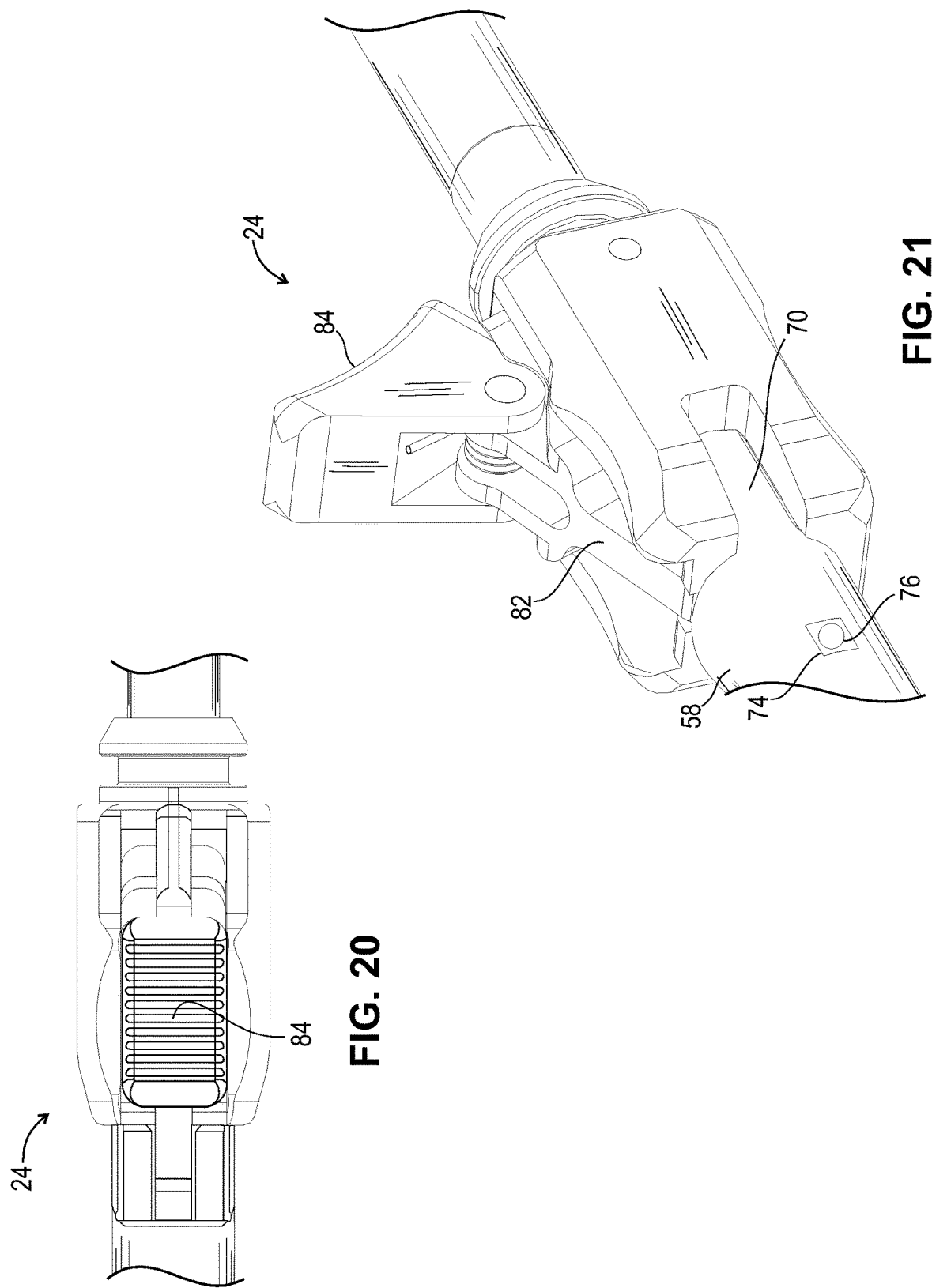

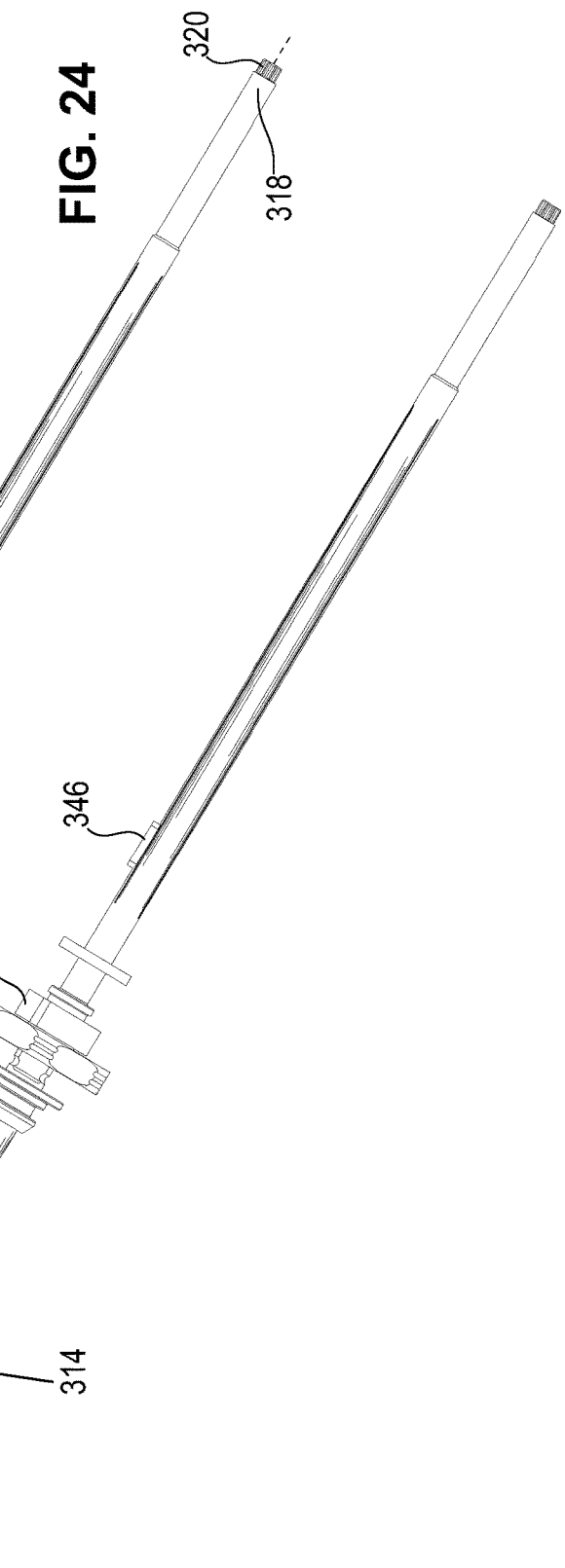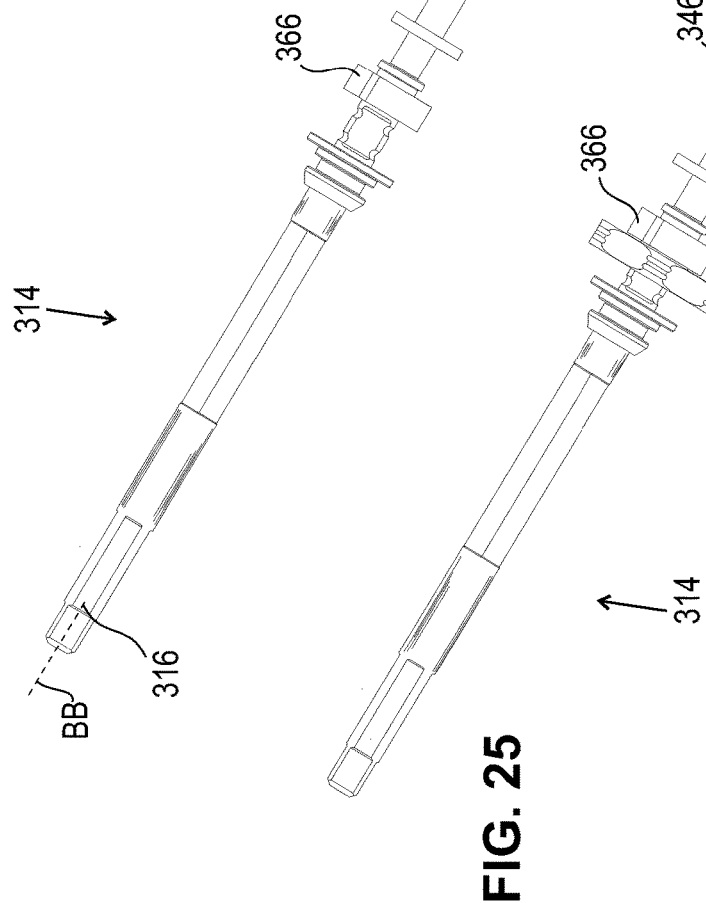

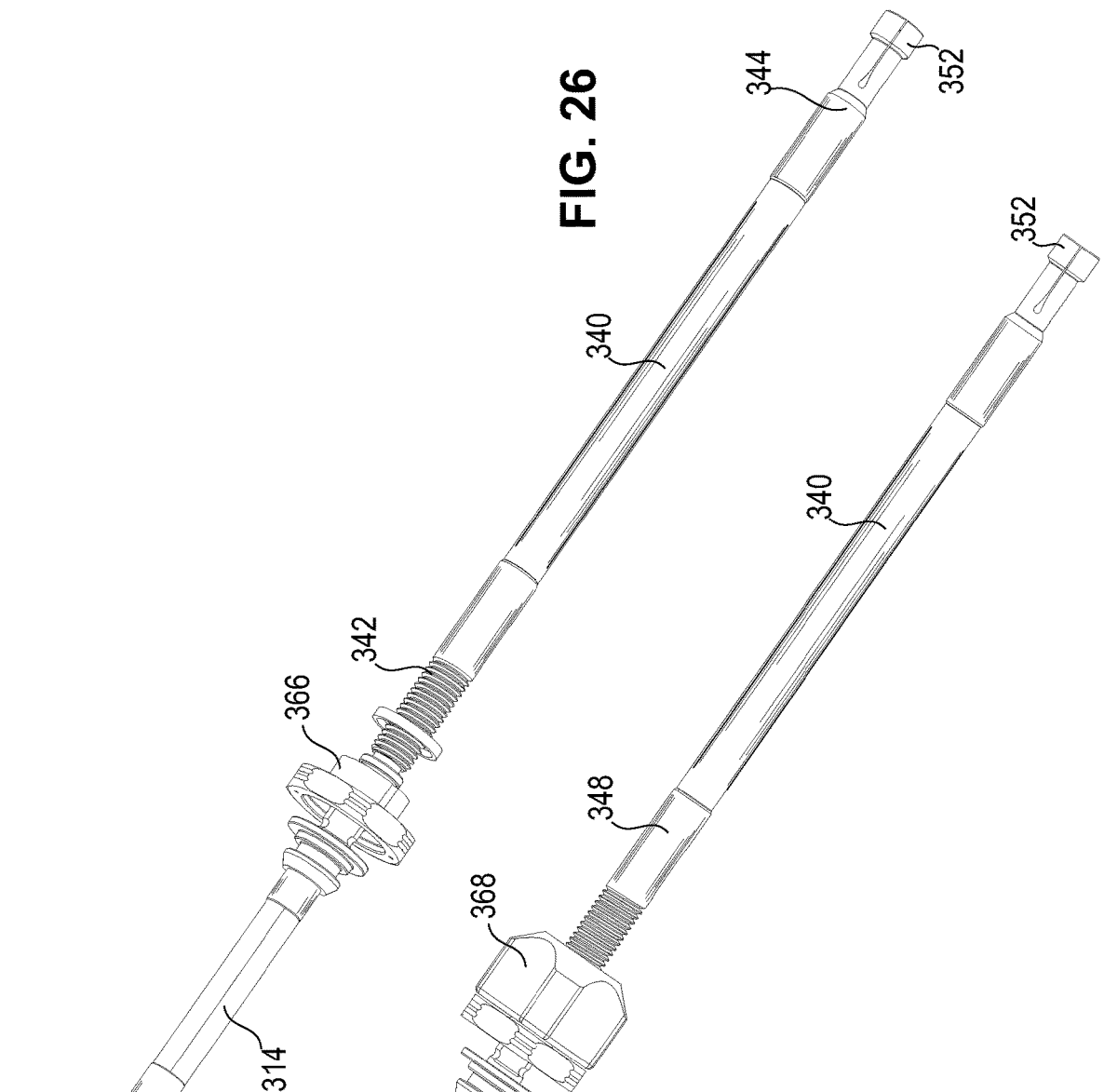
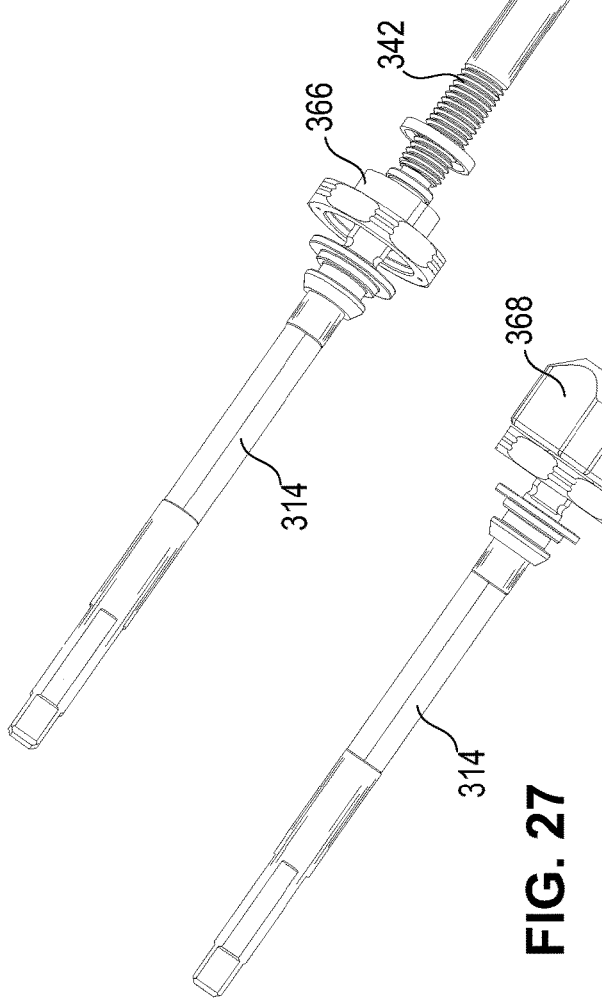

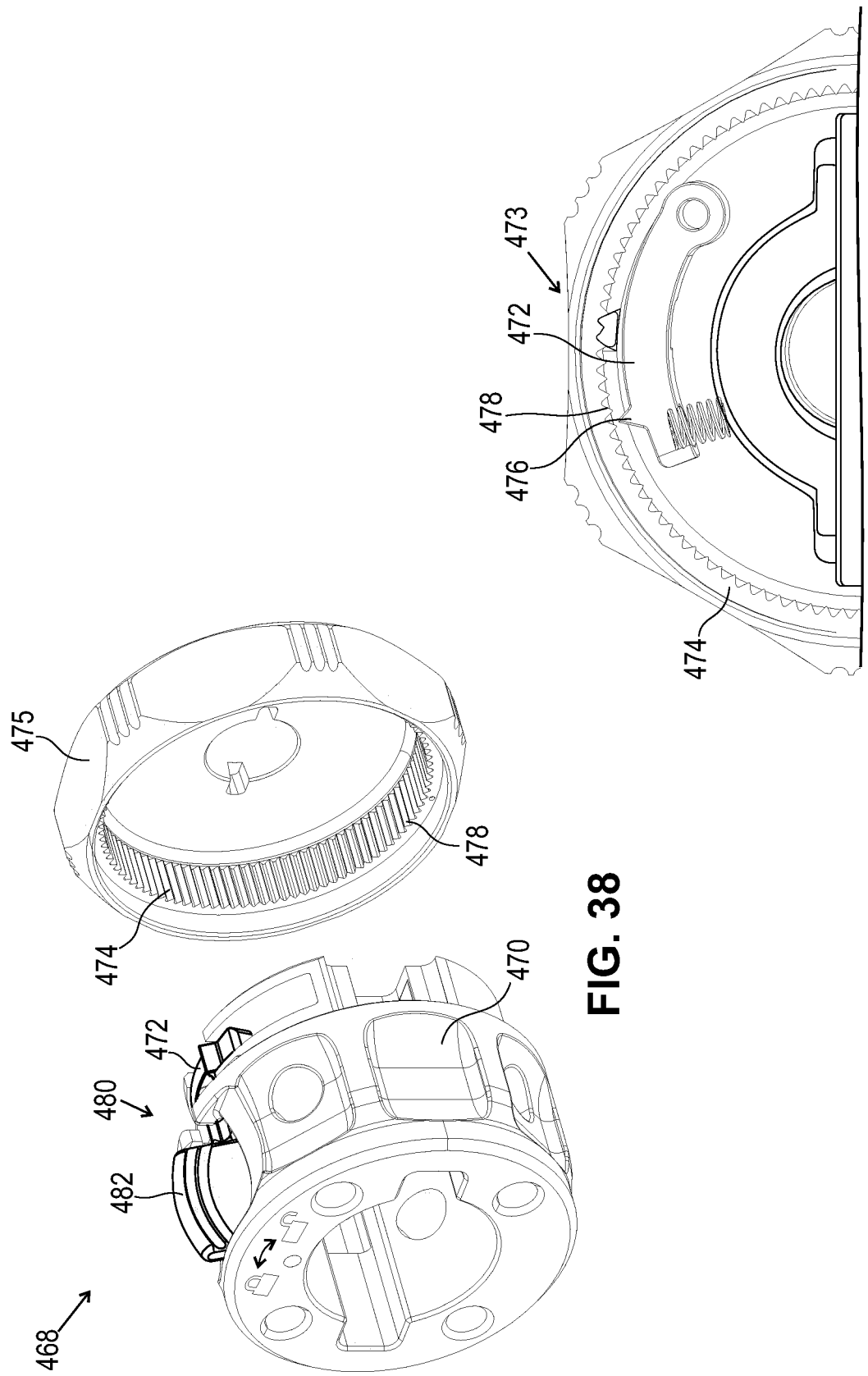

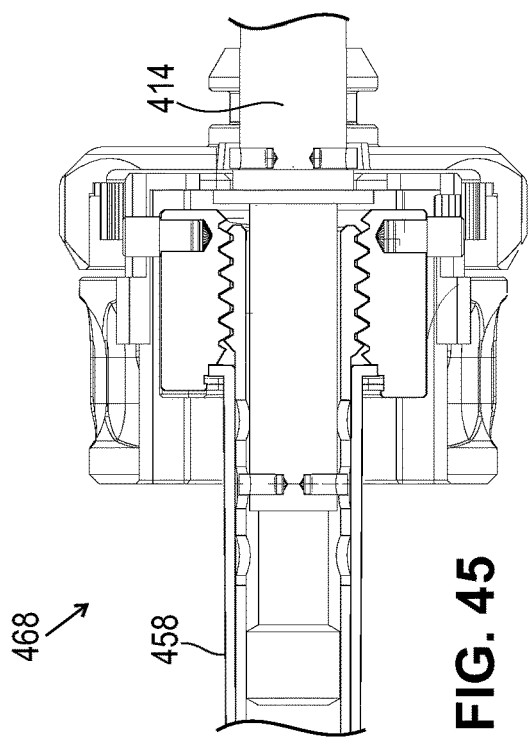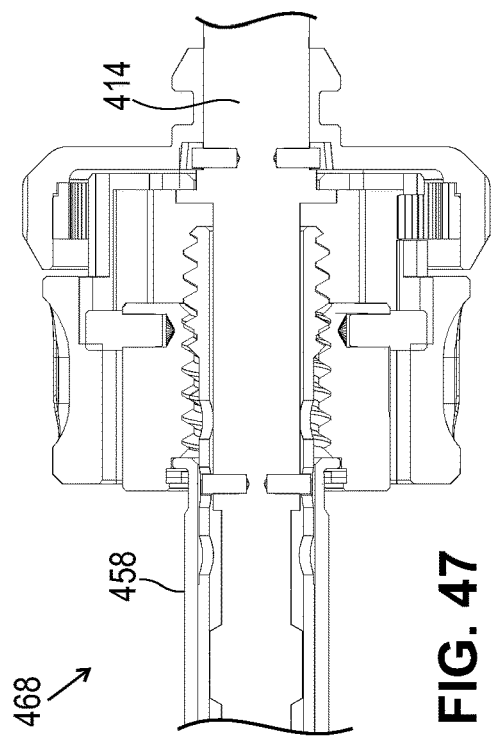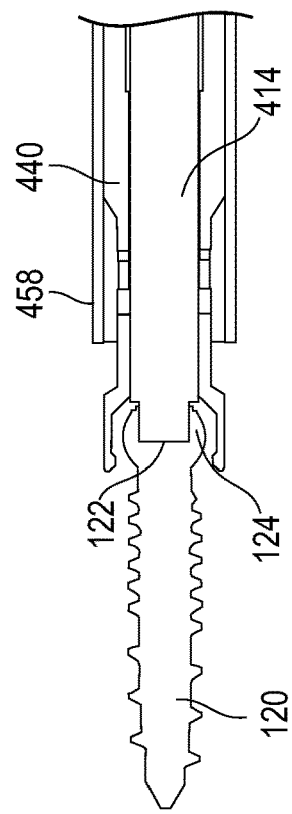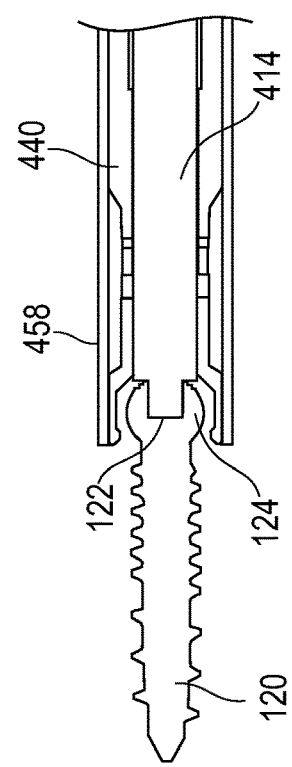

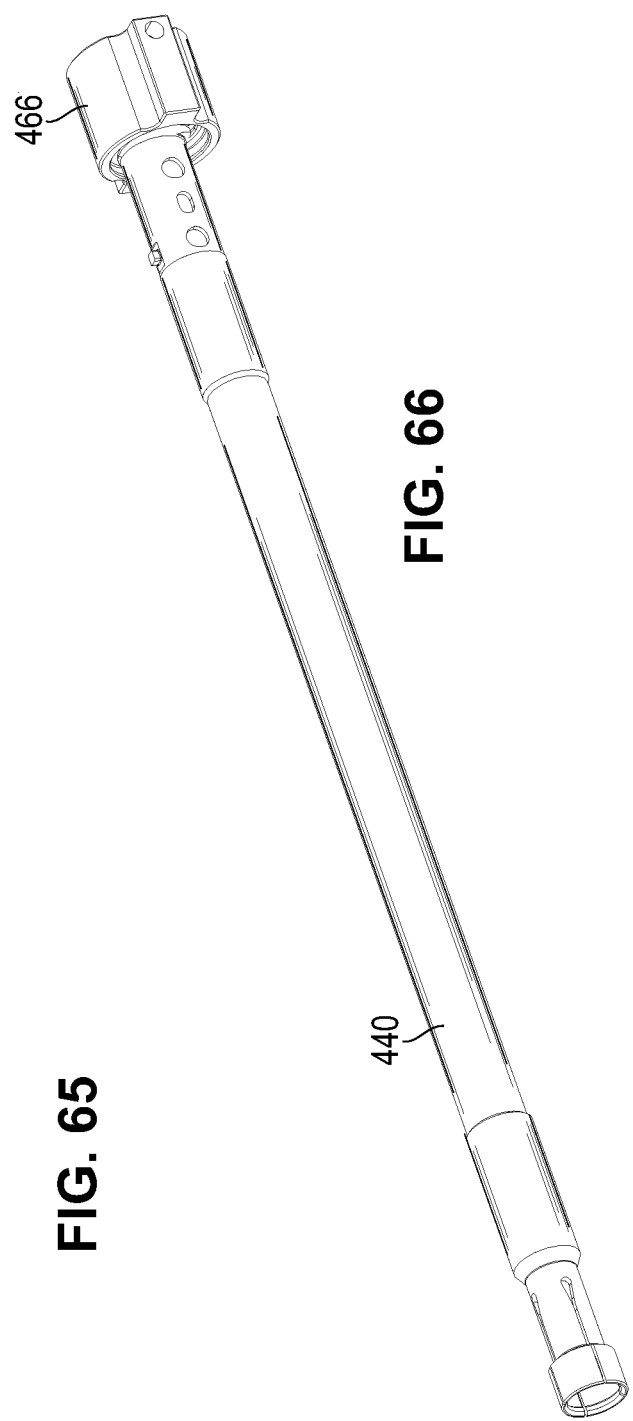

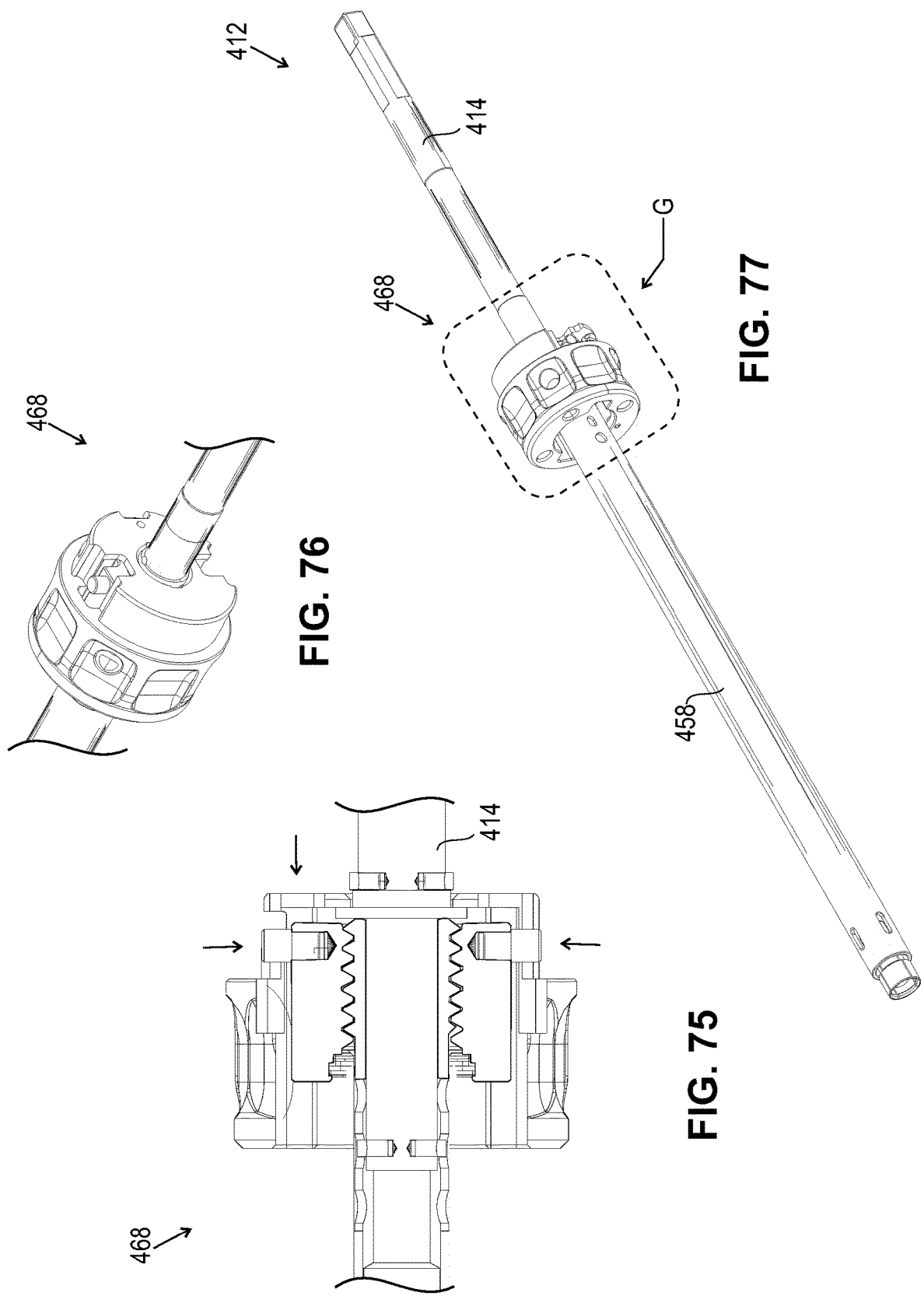

SURGICAL INSTRUMENT AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument includes a first member defining a longitudinal axis and including a first mating surface engageable with a second mating surface of a fastener. A second member includes an expandable portion. A third member is engageable with the expandable portion to releasably capture the fastener. A first lever is connected to the first member and a second lever is connected with the first lever via a pivot. The levers are rotatable relative to the longitudinal axis between a non-locked orientation and a locked orientation such that the pivot is rotatable past axial alignment to fix position of the first member relative to the fastener. In some embodiments, systems, spinal constructs, implants and methods are disclosed.

In some embodiments, the surgical instrument includes a driver defining a longitudinal axis and is engageable with a head of a screw shank. A first sleeve includes a collet. A second sleeve is engageable with the collet to releasably capture the head. A first link is connected to the driver. A compressible member is disposed between the first link and the driver. A second link is connected with the first link via a pivot. The links are rotatable relative to the longitudinal axis between a non-locked orientation and a locked orientation such that the pivot is rotatable past axial alignment to fix position of the driver relative to the head.

In some embodiments, the surgical instrument includes a driver defining a longitudinal axis and is engageable with a head of a screw shank. A first sleeve includes a collet. A second sleeve is engageable with the collet to releasably capture the head. An actuator is connected with the first sleeve and the second sleeve such that the first sleeve is axially translatable relative to the second sleeve between a non-locked orientation and a locked orientation to fix position of the driver relative to the head. The actuator includes a ratchet or a clutch such that the actuator is rotatable about the longitudinal axis in a first direction and prevented from rotation about the longitudinal axis in a second opposite direction.

BRIEF DESCRIPTION OF THE DRAWINGS

The present disclosure will become more readily apparent from the specific description accompanied by the following drawings, in which:

FIG. 7 is a cross section view of the components shown in detail A in FIG. 6;

FIG. 8 is a break away cross section view of components shown in detail B in FIG. 7;

FIG. 9 is a cross section view of the components shown in FIG. 1;

FIG. 10 is a break away cross section view of components shown in detail C in FIG. 9;

FIG. 20 is a break away view of components shown in FIG. 1;

FIG. 21 is a break away view of components shown in FIG. 1;

FIG. 24 is a perspective view of components shown in FIG. 23;

FIG. 25 is a perspective view of components shown in FIG. 23;

FIG. 26 is a perspective view of components shown in FIG. 23;

FIG. 27 is a perspective view of the components shown in FIG. 23;

FIG. 38 is a perspective view of components shown in FIG. 34 with parts separated;

FIG. 39 is a break away cross section view of components shown in FIG. 38;

FIG. 44 is a break away cross section view of components shown in FIG. 34;

FIG. 45 is a break away cross section view of components shown in FIG. 34;

FIG. 46 is a break away cross section view of components shown in FIG. 34;

FIG. 47 is a break away cross section view of components shown in FIG. 34;

FIG. 65 is a break away cross section view of components shown in FIG. 34;

FIG. 66 is a perspective view of components shown in FIG. 34;

FIG. 75 is a break away cross section view of components shown in FIG. 34;

FIG. 76 is a perspective view of components shown in FIG. 34;

FIG. 77 is a break away view of components shown in detail G in FIG. 76;

DETAILED DESCRIPTION

Figure 1:
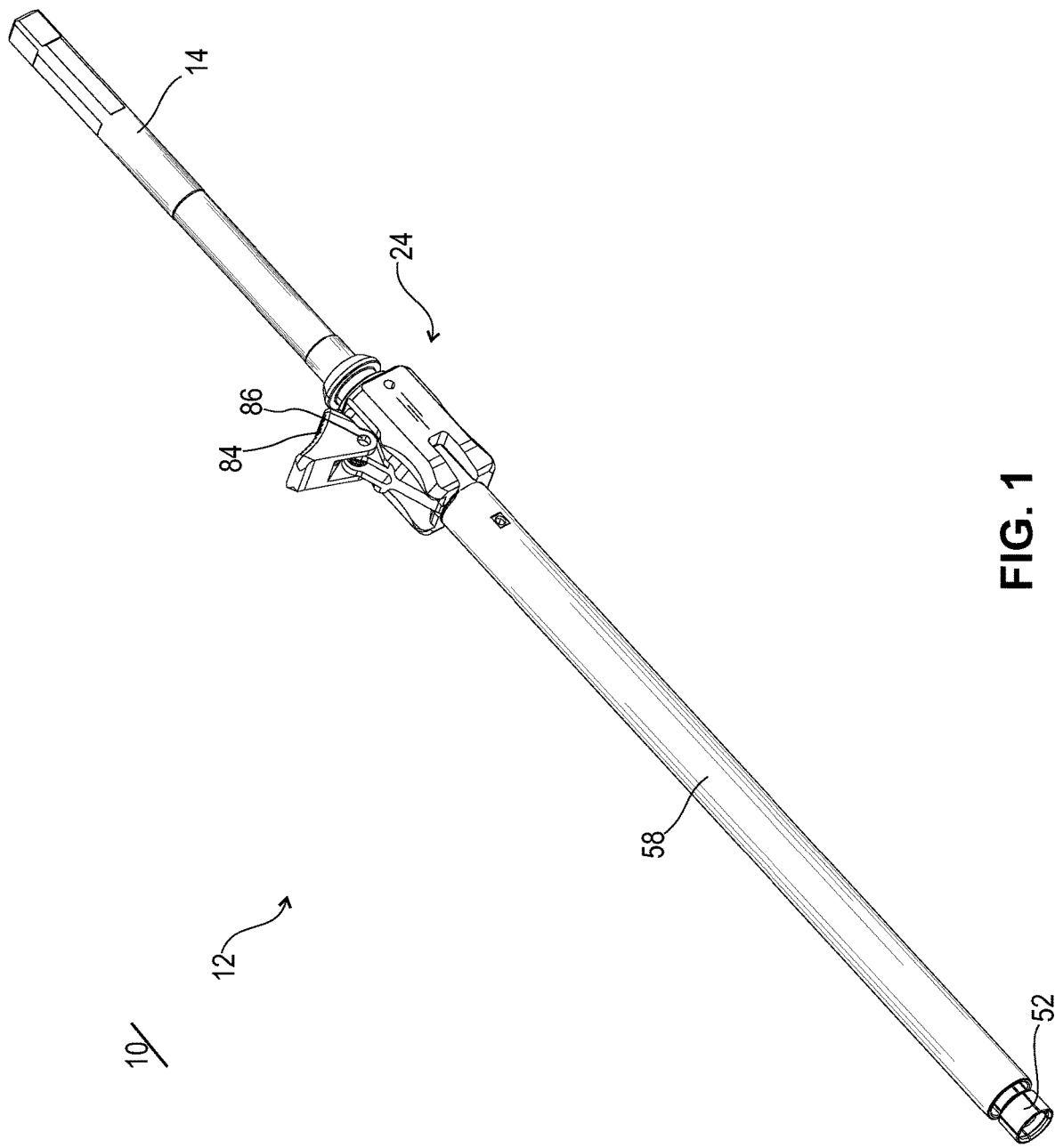
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system and a method for treating a spine. In some embodiments, the systems and methods of the present disclosure include medical devices having surgical instruments and implants that are employed with a surgical treatment, for example, with a cervical, thoracic, lumbar and/or sacral region of a spine. In some embodiments, the present surgical system includes a surgical driver configured to engage, retain and tension a spinal implant, for example, a bone fastener. In some embodiments, the present surgical system includes a surgical driver that engages, captures and/or interfaces with a spinal implant and has one or more lock elements to prevent undesirable loosening, toggle, offset and/or, connection and misalignment of the spinal implant with the driver. In some embodiments, the one or more lock elements include at least one lever and a compressible member. In some embodiments, the one or more lock elements include a ratchet or a clutch mechanism.

In some embodiments, the present surgical system includes a surgical instrument, for example, a surgical driver configured for use with surgical navigation. In some embodiments, the surgical driver is configured for engagement with a spinal implant, for example, a bone screw. In some embodiments, the surgical driver includes an over center toggle lock. In some embodiments, the surgical driver is configured to fix a location of a screw drive, for example, a six point mating surface relative to a collet of the surgical driver to prevent the bone screw from engaging the driver in an undesirable offset orientation, for example, to avoid misalignment and/or undesirable navigation accuracy. In some embodiments, the surgical driver is configured to retain the bone fastener to prevent the bone fastener from loosening from the driver during use.

In some embodiments, the present surgical system includes a surgical driver having an over-center toggle lock configured to reduce the potential for a bone fastener to seat in the surgical driver in an offset orientation by fixing the location of the screw driver relative to a collet of the surgical driver. In some embodiments, a locking mechanism of the surgical driver prevents the bone fastener from loosening during use. In some embodiments, the locking mechanism is configured to lock and unlock via a quick release lever to disengage the bone fastener. In some embodiments, the locking mechanism facilitates quick release and reduces undesirable noise factors.

In some embodiments, the present surgical system includes a surgical driver having a proximal end that includes a lock lever and a distal end that includes a collet and a screw drive. In some embodiments, the distal end of the surgical driver is configured for engagement with a bone screw. In some embodiments, the bone screw is configured to engage the screw driver and the collet simultaneously and the lock lever is depressed to engage the bone screw with the driver. In some embodiments, the surgical driver employs a push button of the lever to lock and disengage the bone screw from the surgical driver. In some embodiments, the surgical driver includes an over-center toggle lock mechanism to engage, retain, and tension the bone screw to the surgical driver.

In some embodiments, the present surgical system includes a surgical driver having an over-center toggle lock mechanism. In some embodiments, the over-center toggle lock mechanism is configured to engage, retain, and tension a bone screw shank to the surgical driver. In some embodiments, the lock mechanism includes a locking lever depressible to lock the bone screw shank to the surgical driver and a release lever depressible to release the bone screw shank from the surgical driver. In some embodiments, the locking lever is depressible relative to, for example, past a linkage mechanism top dead center to prevent the locking mechanism from undesirable release and/or self-reverse. In some embodiments, the locking lever is depressible past a linkage mechanism top dead center by about 1 mm. In some embodiments, the over-center toggle lock mechanism includes a compressible member. In some embodiments, the over-center toggle lock mechanism cannot translate past top dead center, creating an anti-reverse linkage geometry, unless one of the linkage members changes in length.

In some embodiments, the present surgical system includes a surgical driver having an over-center toggle lock mechanism and a compressible member. In some embodiments, the compressible member includes a plurality of washers, for example, spring washers disposed in a stacked orientation. In some embodiments, the compressible member includes one or more coil springs, live springs, compliant elastomer materials, or flexible links. In some embodiments, the compressible member provides deflection for the over-center mechanism to translate past top dead center while creating a force to tension the bone screw shank to the driver to resist bone screw toggle including deflection of the bone screw relative to an axis of the surgical driver. In some embodiments, this configuration avoids reduction in navigation accuracy. In some embodiments, the spring washers are disposed within a cavity of the surgical driver to create a tensioning force, for example, about 300 lbf. In some embodiments, the over-center toggle mechanism is oriented with the surgical driver to facilitate low input force by a user to tension the surgical driver. In some embodiments, the over-center toggle lock mechanism is configured for use for engaging, retaining, and tensioning additional implants, for example, inter body devices.

In some embodiments, the present surgical system includes a surgical driver configured for use with surgical navigation and engagement with a bone screw such that the surgical driver includes a ratchet, for example, a lock sleeve. In some embodiments, the lock sleeve fixes a screw driver relative to a collet of the surgical driver, as described herein. In some embodiments, the ratchet includes a roller clutch that fixes a screw driver relative to a collet of the surgical driver, as described herein. In some embodiments, the ratchet prevents accidental loosening and off-axis alignment of the bone screw. In some embodiments, the surgical driver including a ratchet provides a continuous and/or infinitesimal rotational lock, for example, including selected angular orientations. In some embodiments, the selected angular orientation can include an angular increment selected from a range of greater than 0 through 20 degrees. In some embodiments, the selected angular increment can include about 2, 3, or 4 angular degrees.

In some embodiments, the present surgical system includes a surgical driver configured for use with surgical navigation and engagement with a bone screw such that the surgical driver includes an active ratchet lock that fixes a screw driver relative to a collet sleeve of the surgical driver, as described herein. In some embodiments, the active lock prevents loosening of a bone screw engaged with the surgical driver. In some embodiments, the active lock is configured to prevent an actuator, for example, a knob of the surgical driver from undesirable loosening after tightening, engaging and/or interface of a bone screw with the surgical driver. In some embodiments, the surgical driver having an active ratchet lock includes a collet sleeve fixed relative to a screw driver to prevent misloading a bone screw with the surgical driver. In some embodiments, the surgical driver having an active ratchet lock restricts translation between the screw driver and the collet sleeve to prevent misalignment and/or undesirable assembly between the surgical driver and the bone screw. In some embodiments, the surgical driver having an active ratchet lock prevents the collet sleeve from translating forward or backward to avoid mis-assembly of the bone screw with the surgical driver. In some embodiments, the surgical driver includes an actuator having a counter-torque knob to facilitate increasing torque and/or tightening for engagement and/or interface of a bone screw with the surgical driver. In some embodiments, the active ratchet lock provides a continuous and/or infinitesimal rotational lock, for example, including selected angular orientations, as described herein. For example, if undesirable loosening of the bone screw from the surgical driver occurs, the active ratchet lock rotationally locks the surgical driver in increments of 3.6 angular degrees.

In some embodiments, the present surgical system includes a surgical driver configured for use with an end effector of a robotic arm to facilitate implantation with the robotic arm. In some embodiments, the surgical driver is guided through the end effector for a guide-wireless screw insertion. In some embodiments, the surgical instrument includes a robot screw driver employed with robotic and/or navigation guidance, which may include an image guide.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-21, there are illustrated components of a spinal implant system 10, in accordance with the principles of the present disclosure.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, for example, a bone fastener, at a surgical site of a patient, which includes, for example, a spine. In some embodiments, the spinal implant can include one or more components of one or more spinal constructs, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, for example, a surgical driver 12, as shown in FIGS. 1-4. Surgical driver 12 is configured to engage, capture and/or interface with a spinal implant, for example, a bone fastener 120, and is configured to prevent undesirable loosening, toggle, offset and/or, connection and misalignment of bone fastener 120 with surgical driver 12, as described herein.

Figure 3:
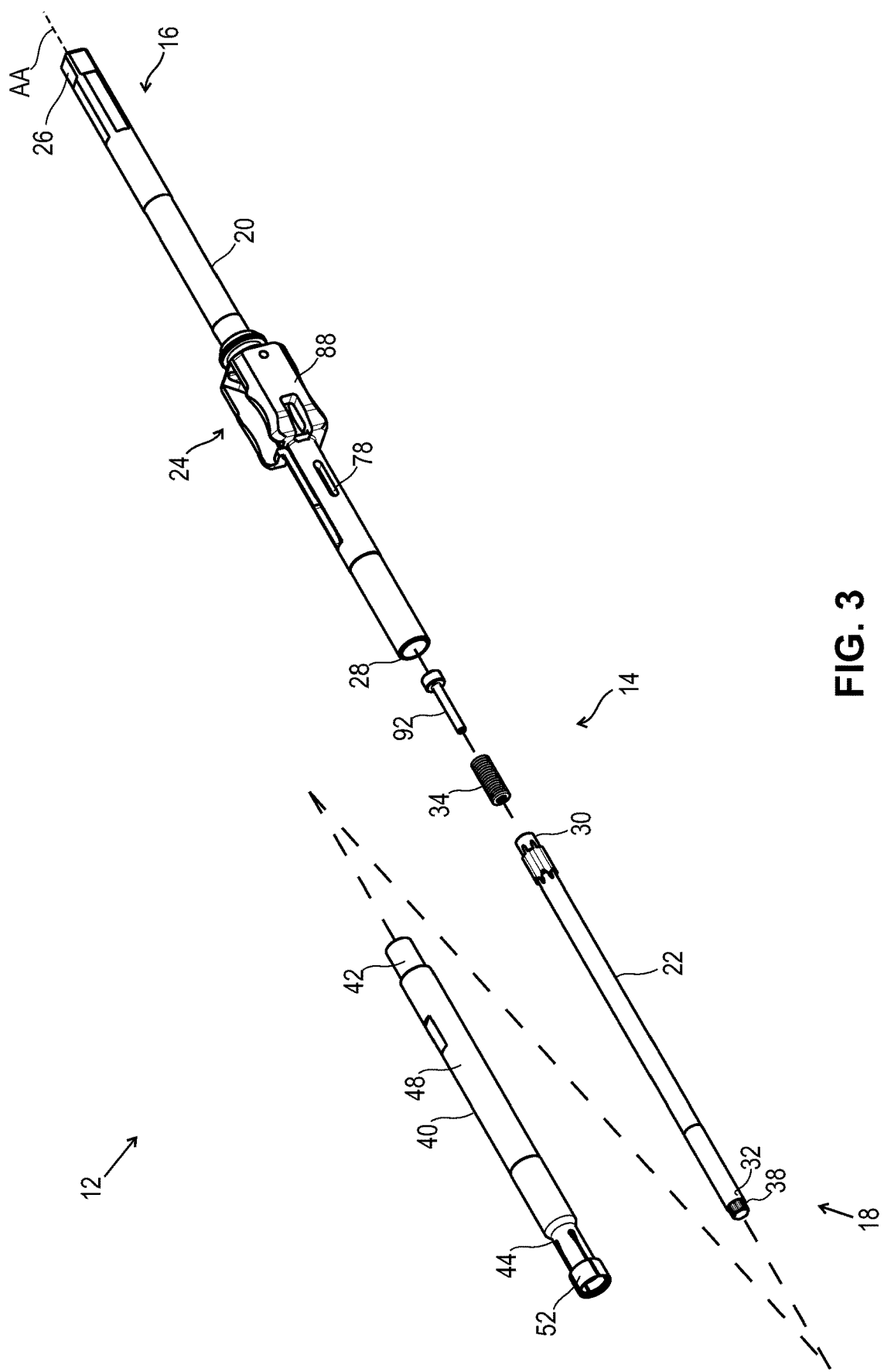
FIG. 3 a perspective view of the components shown in FIG. 1 with parts separated.
Figure 4:
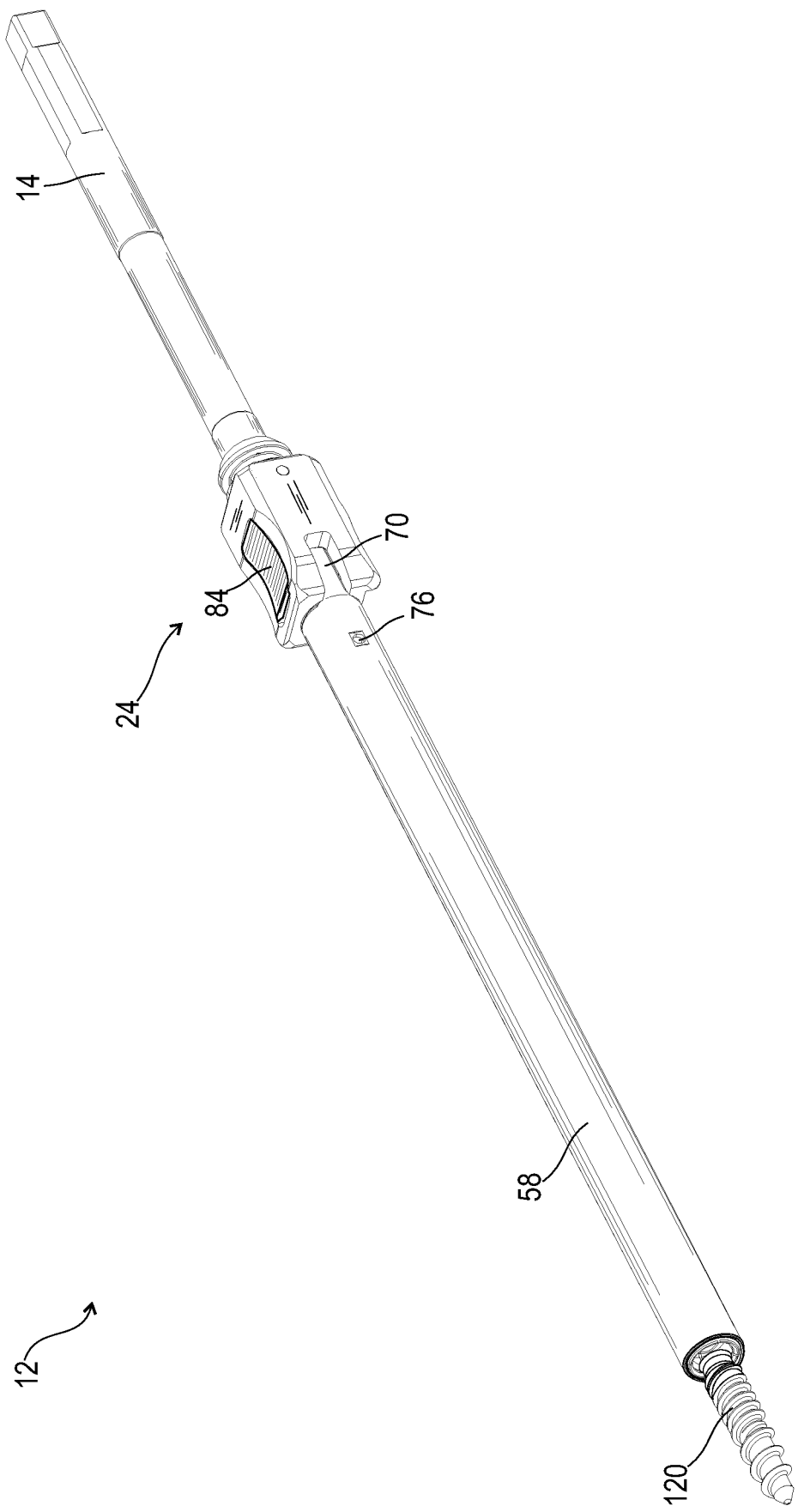
FIG. 4 is a perspective view of the components shown in FIG. 1.

Surgical driver 12 includes a member, for example, a driver shaft 14 extending along a longitudinal axis AA between a proximal end 16 and a distal end 18, as shown FIG. 3. In some embodiments, shaft 14 may have different cross-sections including square, hexagonal, polygonal, triangular, star or hexalobe. Shaft 14 may have various surface configurations, for example, smooth, rough, arcuate, undulating, porous, semi-porous, dimpled, polished and/or textured.

Shaft 14 includes a first section 20 disposed at end 16 and a second section 22 disposed at end 18. Sections 20, 22 are configured for connection to form shaft 14. A portion of section 20 is configured for engagement with an actuator 24, as described herein. Section 20 includes an end 26 and an end 28. End 26 is configured for engagement with a surgical tool and end 28 is configured for engagement with a mating end 30 of section 22. End 30 includes a six point, for example, a star shaped configuration, as shown in FIG. 8 (see, for example, a similar star shaped configuration of Torx® (Acument Global Technologies, Inc., Sterling Heights, Michigan, USA)). End 30 is configured for engagement with components of a lever 82, which includes link 81 and a compressible member, for example, spring washers 34 that are disposable about a shaft 92 of link 81, described herein. End 30 is configured to transfer torque while allowing axial translation. In some embodiments, end 30 includes an oval, straight, knurl, and/or keyway configuration.

Figure 5:
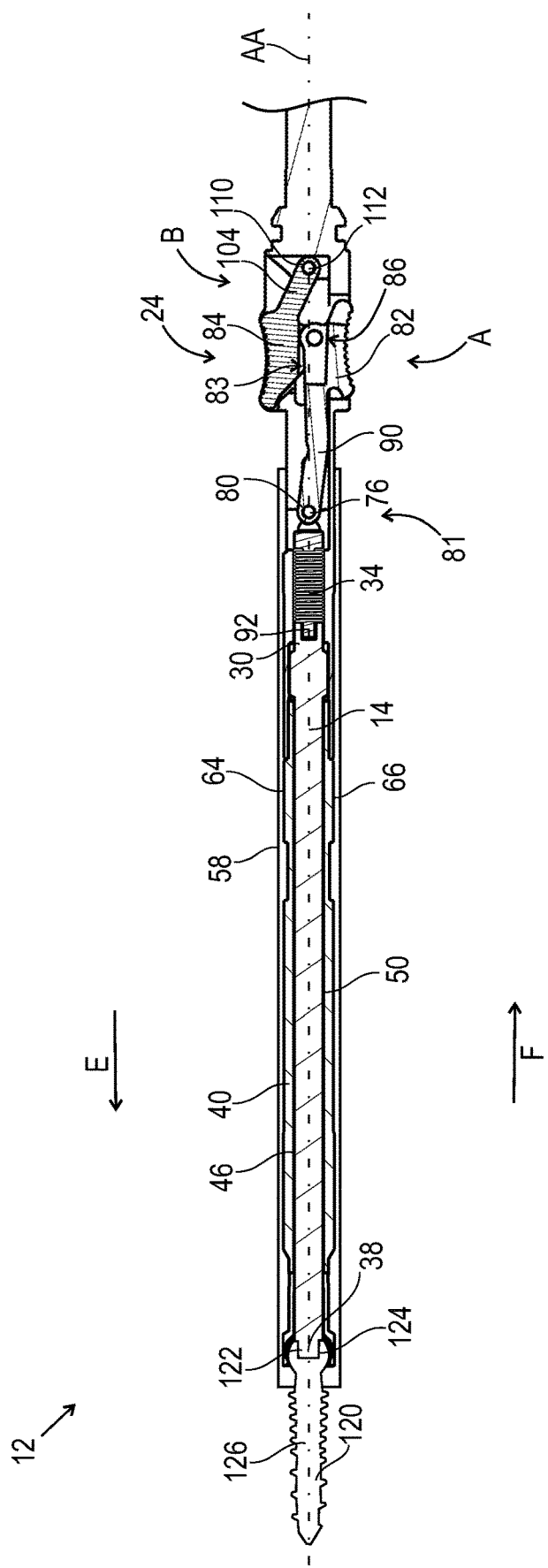
FIG. 5 is a cross section view of components shown in FIG. 1.
Figure 6:
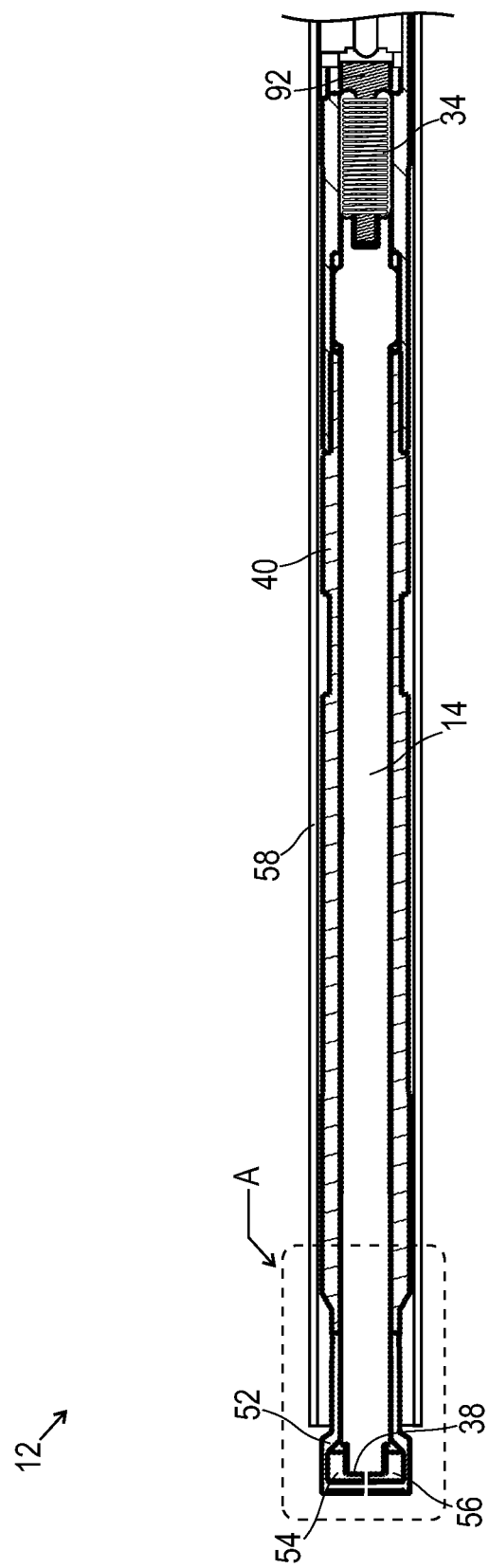
FIG. 6 is a cross section view of the components shown in FIG. 1.
Figure 11:
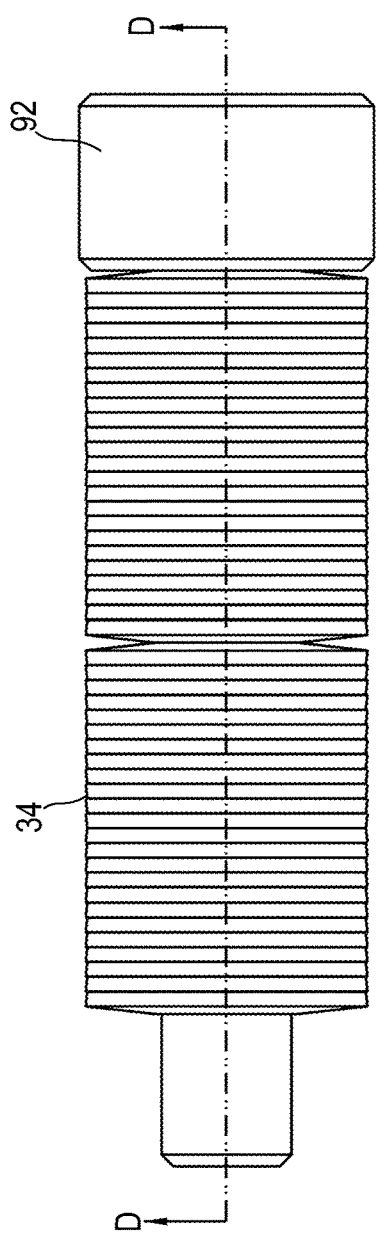
FIG. 11 is a side view of components shown in FIG. 3.
Figure 12:
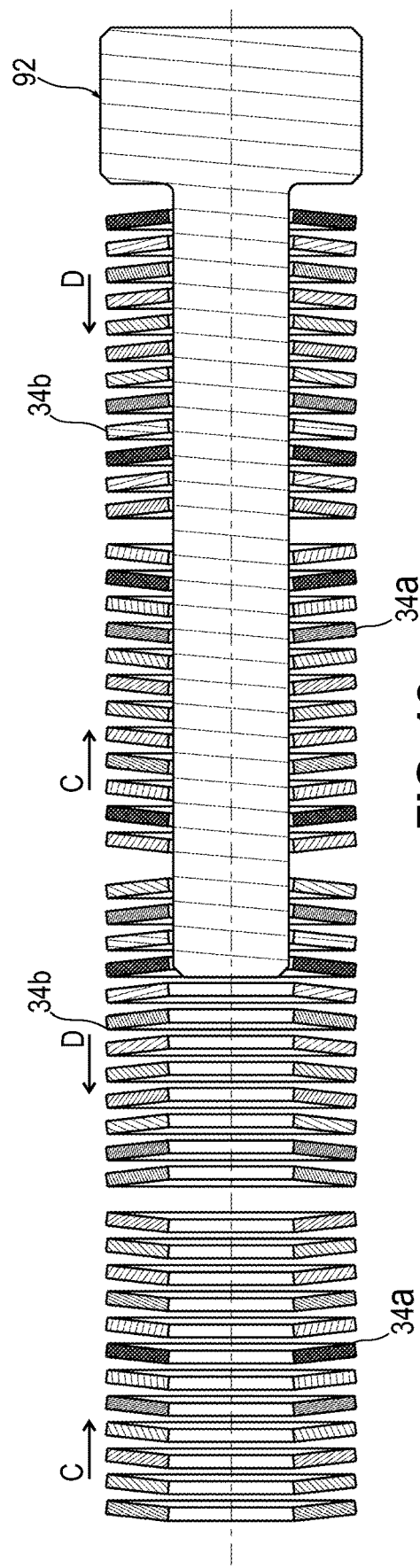
FIG. 12 is an enlarged cross section view of components shown in detail D in FIG. 11.
Figure 14:
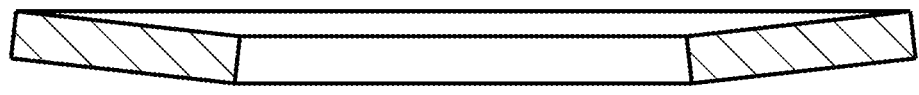
FIG. 14 is a side view of the component shown in FIG. 13.
Figure 13:
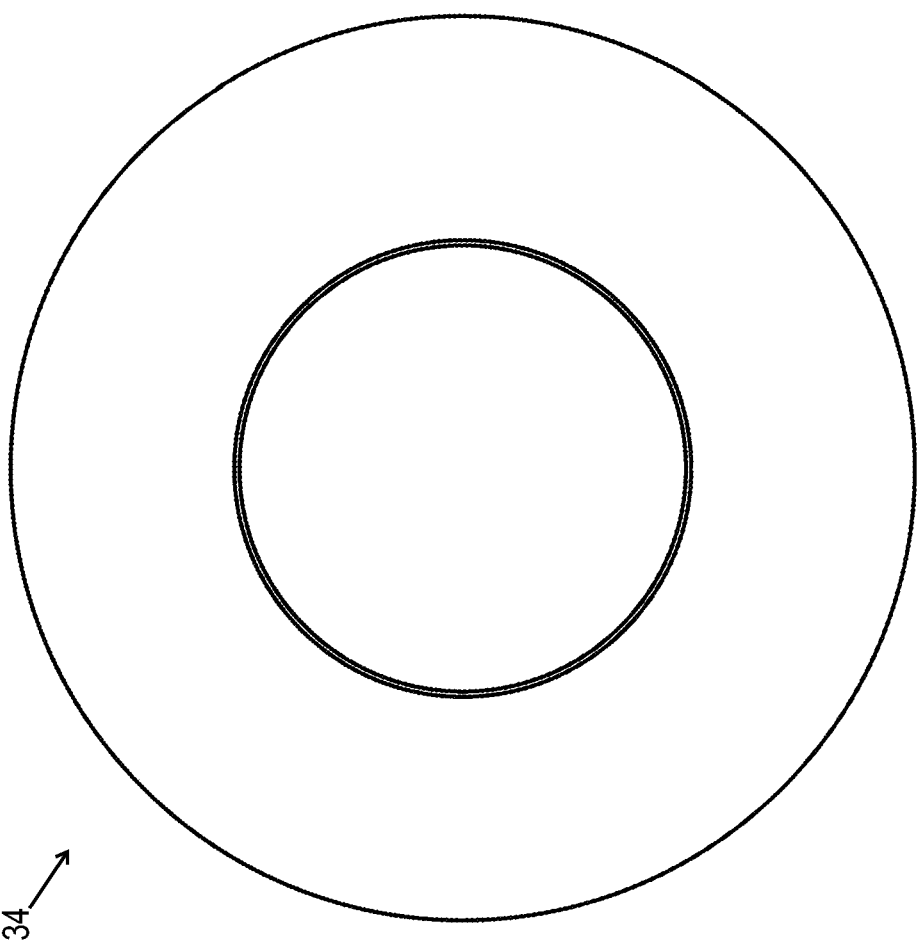
FIG. 13 is a break away view of a component shown in FIG. 11.

Section 22 includes an end 32. End 32 is configured for engagement with an implant, for example, bone fastener 120. End 32 includes a mating surface 38 configured for engagement with a mating surface 122 of bone fastener 120, as shown in FIG. 5. Mating surface 38 includes a six point, for example, a star shaped configuration (see, for example, a similar star shaped configuration of Torx® (Acument Global Technologies, Inc., Sterling Heights, Michigan, USA)). In some embodiments, ends 30, 32 may have various surface configurations, including, smooth, rough, arcuate, undulating, porous, semi-porous, dimpled, polished and/or textured.

Surgical driver 12 includes a member, for example, a sleeve 40 configured for disposal of section 22 of shaft 14. Sleeve 40 extends between an end 42 and an end 44 along axis AA. Sleeve 40 includes an inner surface 46 and an outer surface 48. Surface 46 defines a passageway 50 coaxial with axis AA and is configured for disposal of section 22 of shaft 14, as shown in FIG. 5. End 42 is configured for engagement with end 28 of section 20 of shaft 14. In some embodiments, end 42 is configured for engagement with end 28 via a welded interface.

Figure 18:
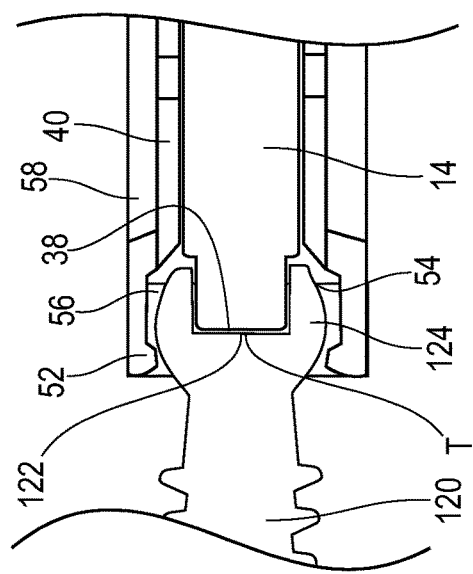
FIG. 18 is a break away cross section view of components shown in detail E in FIG. 17.
Figure 19:
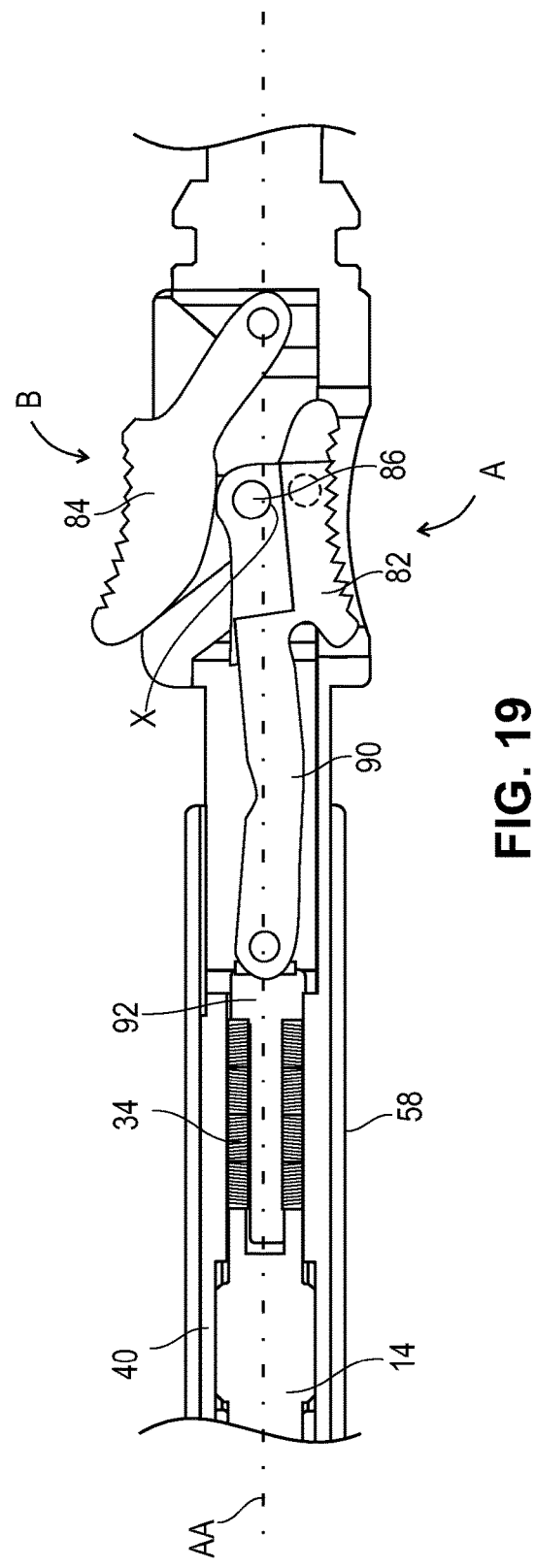
FIG. 19 is a break away cross section view of components shown in detail F in FIG. 17.

End 44 includes an expandable portion, for example, a collet 52. Collet 52 is configured for movement between an expandable configuration and a contractable configuration, as described herein. Collet 52 includes an inner surface 54 that defines a passageway 56 that is configured for engagement with surfaces of a head 124 of bone fastener 120, as shown in FIG. 18. Passageway 56 includes a cylindrical cross-section configuration. In some embodiments, passageway 56 may have various cross section configurations, for example, oval, oblong, triangular, rectangular, square, polygonal, irregular, uniform, non-uniform, variable, tubular and/or tapered.

Shaft 14 axially translates relative to collet 52 and is limited to avoid mis-assembly of bone fastener 120 and ensures that mating surface 38 is fully engaged into bone fastener 120 when collet 52 is engaged. A sleeve 58, described herein, will not cover collet 52 unless mating surface 38 is fully engaged with bone fastener 120 to prevent mis-assembly by the user.

Figure 2:
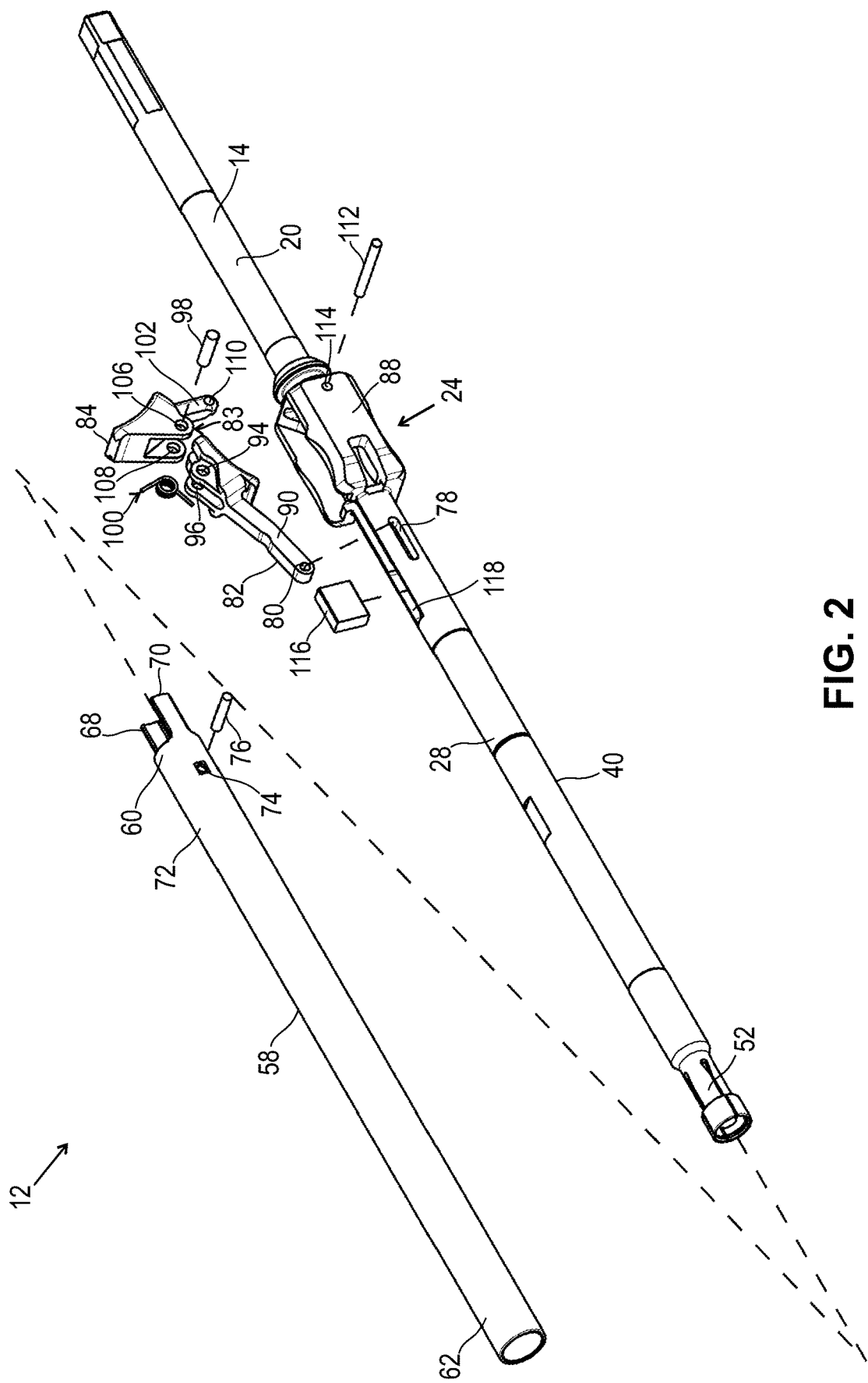
FIG. 2 a perspective view of the components shown in FIG. 1 with parts separated.

Surgical driver 12 includes a member, for example, sleeve 58, as shown in FIG. 2. Sleeve 58 is configured for engagement with collet 52 to releasably capture bone fastener 120. Sleeve 58 extends between a proximal end 60 and a distal end 62 along axis AA. Sleeve 58 includes an inner surface 64 that defines a passageway 66 (FIG. 5) coaxial with axis AA and configured for disposal of sleeve 40. In one embodiment, inner surface 64 may have various surface configurations to enhance engagement with sleeve 40 and/or collet 52, for example, rough, arcuate, undulating, porous, semi-porous, dimpled, polished and/or textured.

End 60 is configured for engagement with section 20 of shaft 14. End 60 includes a surface that defines an arm 68 and an arm 70 configured for engagement with a portion of actuator 24. An outer surface 72 defines an opening 74 configured for disposal of a pin 76 that engages a slot 78 defined from a surface of section 20 of shaft 14 and an opening 80 defined from a surface of a flange 90 of link 81, to facilitate translation of sleeve 58 relative to shaft 14, described herein.

End 62 is configured for engagement with collet 52 such that translation of sleeve 58 in a distal direction causes end 62 to slide over collet 52 to move collet between the expandable configuration to the contractable configuration around head 124 of bone fastener 120 to lock collet 52 with head 124.

Surgical driver 12 includes actuator 24 configured for connection with shaft 14. Actuator 24 includes an over-center toggle lock mechanism which includes lever 82 and a lever 84, shown in FIGS. 2 and 5. Lever 84 is configured for connection with shaft 14 via a pin 112, and lever 84 is configured for connection with lever 82 via a pivot point 86, described herein. Lever 84 includes a locking lever that is depressible to lock head 124 of bone fastener 120 to surgical driver 12, and lever 82 includes a release lever that is depressible to release head 124 of bone fastener 120 from surgical driver 12. Levers 82, 84 are rotatable relative to axis AA between a non-locked orientation, shown by arrow A in FIG. 5 and a locked orientation, shown by arrow B in FIG. 5, such that pivot point 86 is rotatable past axial alignment to fix the position of shaft 14 relative to bone fastener 120 and to prevent release of bone fastener 120 by tensioning shaft 14. In the locked orientation, bone fastener 120 is prevented from loosening and toggle.

Figure 15:
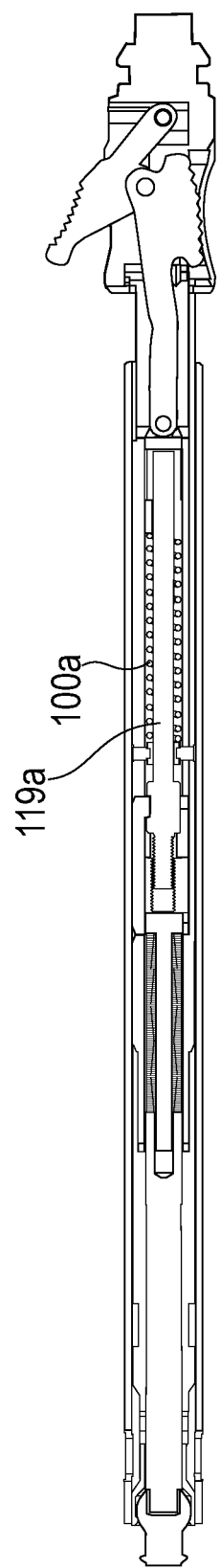
FIG. 15 is a side view of components of one embodiment of a surgical system in accordance with the principles of the present disclosure.
Figure 16:
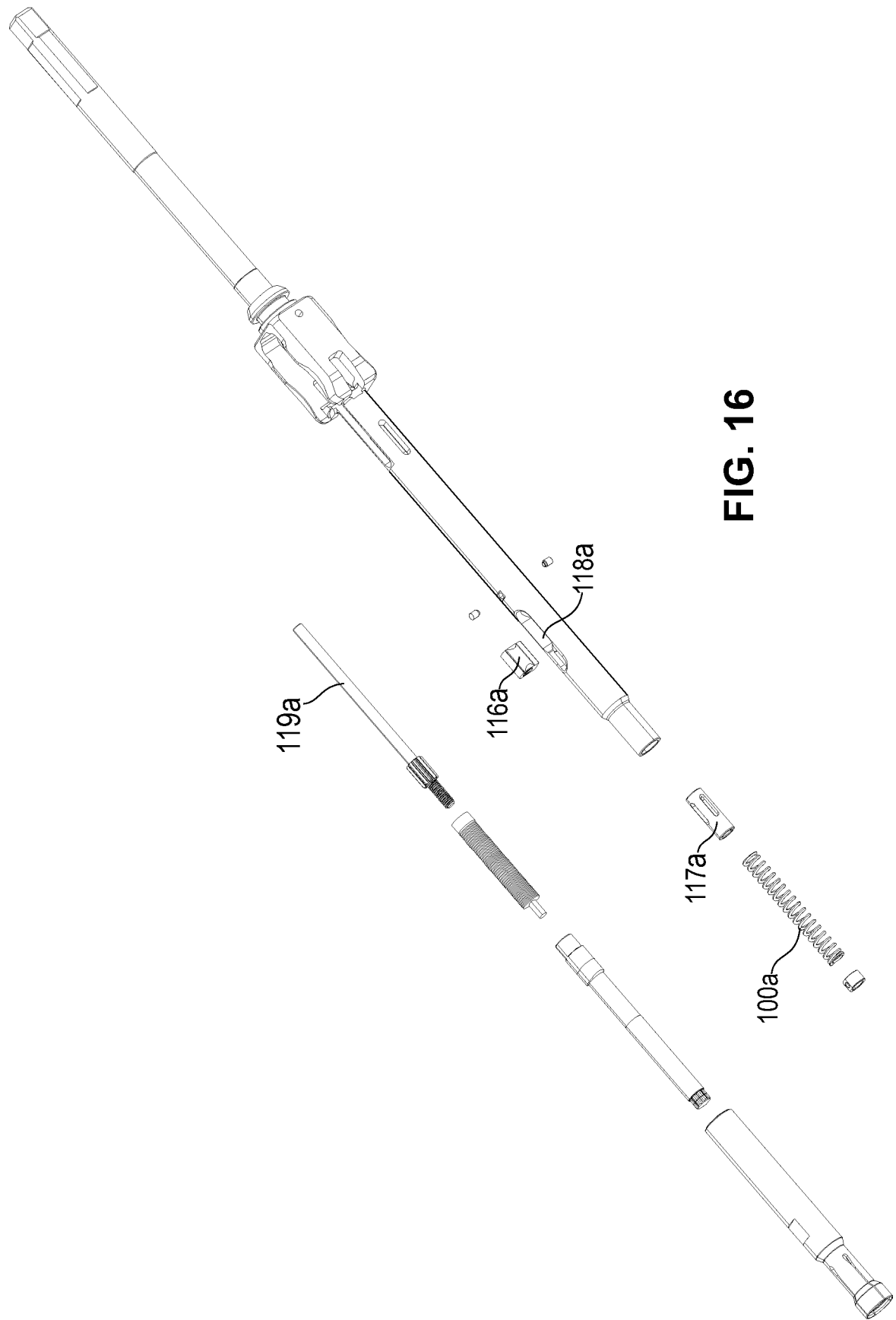
FIG. 16 a perspective view of the components shown in FIG. 15 with parts separated.
Figure 17:
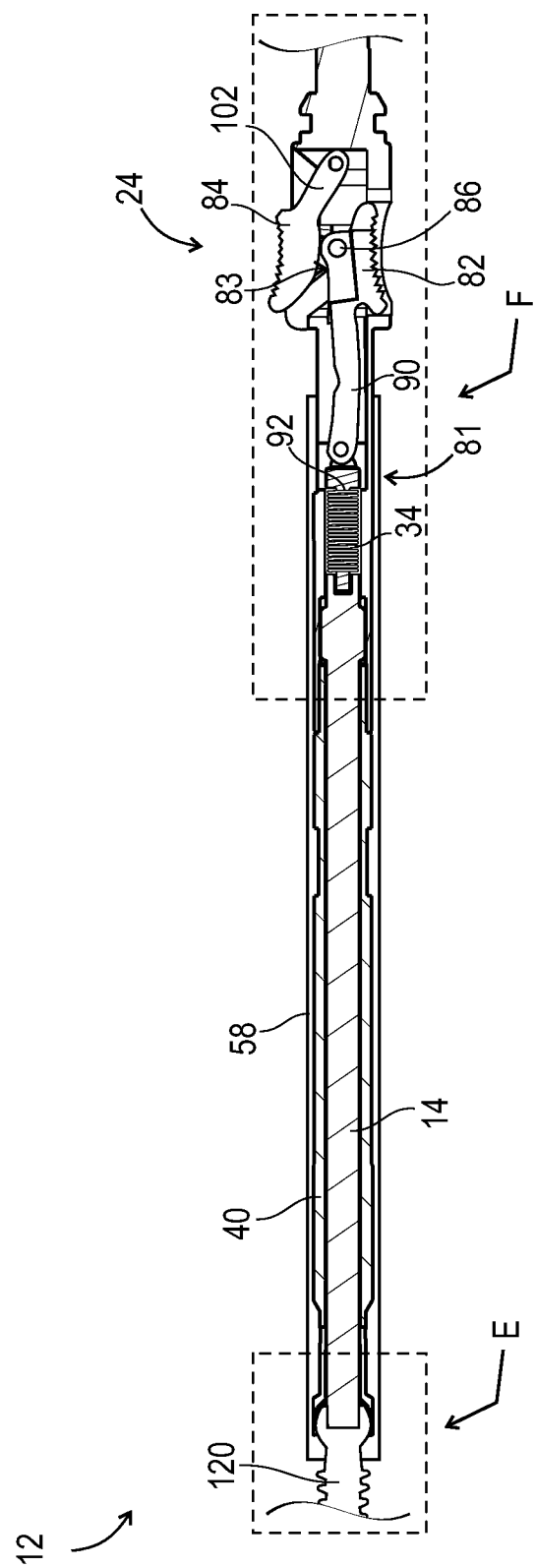
FIG. 17 is a cross section view of the components shown in FIG. 1.

Levers 82, 84 are configured for disposal in a housing 88. Lever 82 includes link 81 including flange 90 and shaft 92, shown in FIGS. 2 and 5. Spring washers 34 are configured for disposal about shaft 92. Flange 90 includes a surface that defines openings 94, 96. Openings 94, 96 are configured for disposal of a pin 98 and a biasing member, for example, a spring 100. Spring 100 is configured for disposal between openings 94, 96 and is configured to apply force against levers 82 and 84, thus maintaining a bias for the over-center toggle lock mechanism while in an unlocked state. In one embodiment, as shown in FIGS. 15 and 16, surgical driver 12 includes a coil spring 100a as an alternative to spring 100. Spring 100a is disposed about an adjustor shaft 119a and is configured to apply force against levers 82 and 84, thus maintaining a bias for the over-center toggle lock mechanism while in an unlocked state.

Lever 84 includes a link 83 connected to link 81 via pivot point 86, as shown in FIGS. 2 and 5. Link 83 includes a surface that define openings 106, 108. Openings 106, 108 are configured for engagement with openings 94, 96 and pin 98 to form pivot point 86. Lever 84 includes an arm 102. Arm 102 includes a surface that defines an opening 110 configured for disposal of pin 112, and pin 112 is configured for disposal within an opening 114 defined from a surface of housing 88 such that lever 84 is engageable with housing 88.

Lever 84 is engageable to dispose levers 82, 84 in the locked orientation. Lever 84 is depressible such that pivot point 86 is rotatable past axial alignment of axis AA/top dead center of surgical driver 12 to fix the position of shaft 14 and to prevent undesirable release and/or self-reverse. For example, pivot point 86 is rotatable to the locked orientation, in the direction of arrow B, translating past axis AA alignment by a distance X, shown in FIG. 19. In some embodiments, lever 84 is depressible such that pivot point 86 is rotatable past axial alignment/top dead center, where distance X is about 1 mm. In some embodiments, pivot point 86 is rotatable past axial alignment, where distance X is in a range of 0.25 through 3 mm. In some embodiments, pivot point 86 cannot translate past top dead center of surgical driver 12, creating an anti-reverse linkage geometry. Lever 82 is engageable to release levers 82, 84 from the locked orientation and to position levers 82, 84 into the non-locked orientation.

Spring washers 34 are disposed between lever 82 and shaft 14 in a stacked configuration, as shown in FIG. 5. Spring washers 34 are configured to maintain tension on shaft 14 when levers 82, 84 are rotatable in the locked orientation to fix shaft 14 with bone fastener 120, and to prevent bone fastener 120 from loosening and toggle. In some embodiments, spring washers 34 provide deflection for the over-center toggle lock mechanism to translate past top dead center while creating a force to tension bone fastener 120 to surgical driver 12 to resist bone fastener 120 toggle including deflection of bone fastener 120 relative to axis AA of surgical driver 12. In some embodiments, this configuration avoids reduction in navigation accuracy.

In some embodiments, spring washers 34 include one or a plurality of conical spring washers 34, as shown in FIGS. 9-14. In some embodiments, the one or a plurality of conical spring washers 34 include a first plurality of washers 34a oriented in a first axial direction, shown by arrows C in FIG. 12, and a second plurality of washers 34b oriented in a second opposite axial direction, shown by arrows D in FIG. 12.

Spring washers 34 are engageable with shaft 14 to maintain tension on shaft 14 with a force in a range of 100 through 1000 pound-force (lbf). In some embodiments, spring washers 34 are engageable with shaft 14 to maintain tension on shaft 14 with a force of 300 lbf. Spring washers 34 are engageable with shaft 14 to resist and/or prevent movement of mating surface 122 of bone fastener 120 with mating surface 38 of shaft 14 relative to axis AA in a selected variational tolerance T in a range of 1 through 5 mm, as shown in FIG. 18. In some embodiments, spring washers 34 are manufactured from steel, including carbon steel, spring steel and stainless steel. In some embodiments, spring washers 34 are manufactured from copper, brass, aluminum, titanium, bronze, zinc, iron and/or rubber. In some embodiments, spring washers 34 alternatively include one or more coil springs, live springs, compliant elastomer materials, or flexible links.

In some embodiments, surgical driver 12 includes an adjustor block 116 configured for disposal within a slot 118 of shaft 14, and is configured for disposal between flange 90 and shaft 92 of lever 82, as shown in FIG. 2. Adjustor block 116 is configured to adjust a gap disposed between flange 90 and shaft 92. In one embodiment, as shown in FIG. 16, surgical driver 12 includes a threaded adjustor block 116a as an alternative to adjustor block 116. A threaded section (not shown) can be rotated for adjustment during manufacturing to adjust the gap between a plunger 117a and spring 100a. In some embodiments, the threaded section is rotated for adjustment only during manufacturing due to a key (not shown) that is configured to cover threaded adjustor block 116a when threaded adjustor block 116a is disposed within a slot 118a. In some embodiments, the threaded section is rotated for adjustment in an operating room by the user. In some embodiments, an adjustor screw (not shown) is substituted for adjustor block 116.

Bone fastener 120 includes head 124 configured for engagement with shaft 14, and an elongated shaft 126 configured for penetrating tissue. Head 124 includes a spherical configuration. Head 124 includes an outer circumferential surface having a substantially spherical configuration. Head 124 includes an inner surface that defines a cavity, for example, mating surface 122. Mating surface 122 is configured for disposal of an instrument and/or tool extension, for example, mating surface 38 of shaft 14, as discussed herein. Mating surface 122 is centrally positioned with respect to head 124. Mating surface 122 is coaxial with axis AA. In some embodiments, mating surface 122 may have various cross-section configurations, for example, oval, oblong, triangular, rectangular, square, star, polygonal, irregular, uniform, non-uniform, variable, tubular and/or tapered. In some embodiments, mating surface 122 may have various surface configurations, for example, smooth and/or surface configurations to enhance engagement with mating surface 38 of shaft 14, for example, rough, arcuate, undulating, porous, semi-porous, dimpled, polished and/or textured.

Elongated shaft 126 has a cylindrical cross section configuration and includes an outer surface having an external thread form. In some embodiments, the thread form may include a single thread turn or a plurality of discrete threads. In some embodiments, other engaging structures may be disposed on elongated shaft 126, for example, a nail configuration, barbs, expanding elements, raised elements and/or spikes to facilitate engagement of elongated shaft 126 with tissue, for example, vertebrae.

In some embodiments, all or only a portion of elongated shaft 126 may have alternate cross section configurations, for example, oval, oblong, triangular, square, polygonal, irregular, uniform, non-uniform, offset, staggered, undulating, arcuate, variable and/or tapered. In some embodiments, the outer surface may include one or a plurality of openings. In some embodiments, all or only a portion of the outer surface may have alternate surface configurations to enhance fixation with tissue for example, rough, arcuate, undulating, mesh, porous, semi-porous, dimpled and/or textured. In some embodiments, all or only a portion of elongated shaft 126 may be disposed at alternate orientations, relative to a longitudinal axis of bone fastener 120, for example, transverse, perpendicular and/or other angular orientations including acute or obtuse, co-axial and/or may be offset or staggered. In some embodiments, all or only a portion of elongated shaft 126 may be cannulated.

In assembly, operation and use, spinal implant system 10, similar to the systems and methods described herein, is employed with a surgical procedure, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

Figure 22:
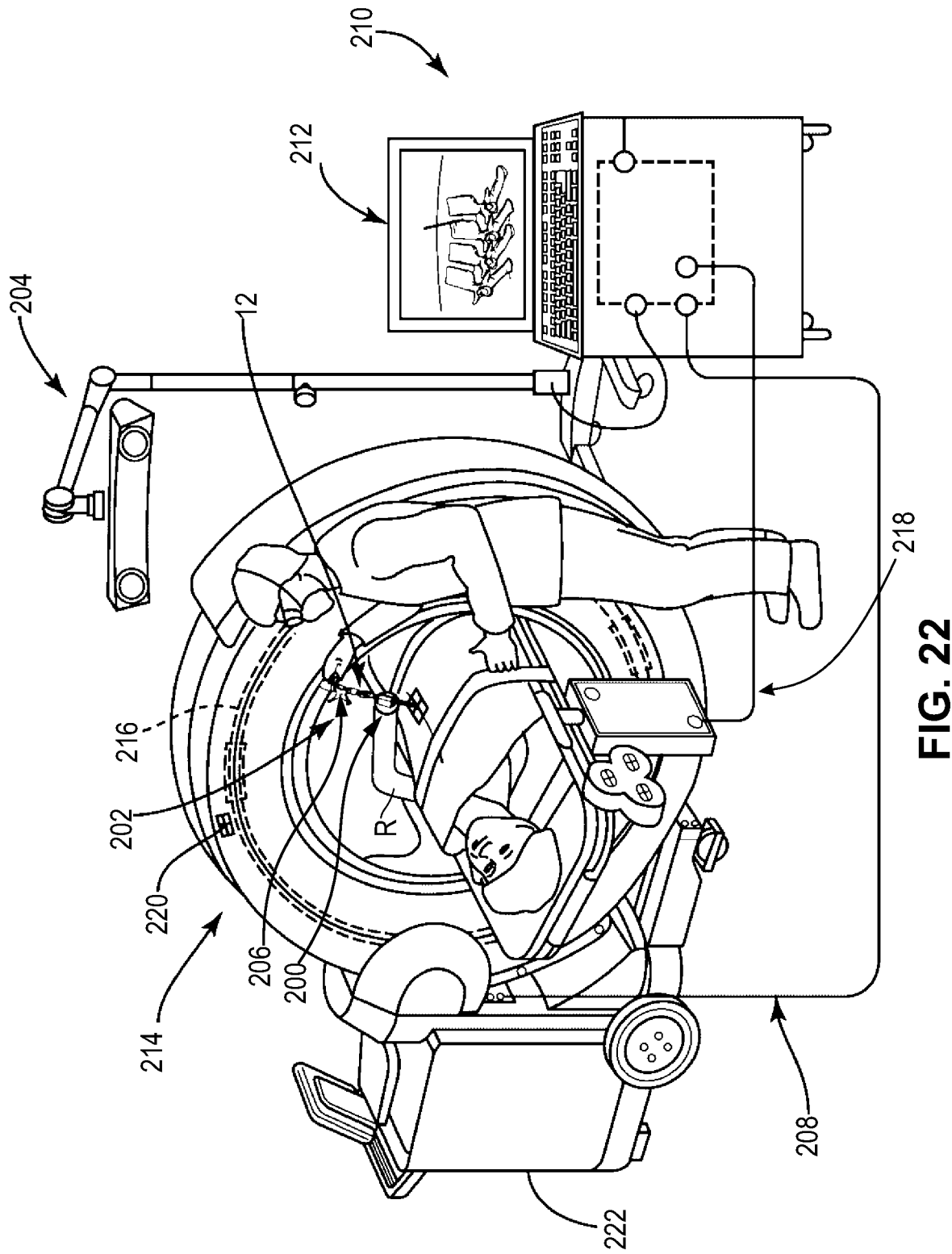
FIG. 22 is a perspective view of components of one embodiment of a surgical system in accordance with the principles of the present disclosure.
Figure 23:
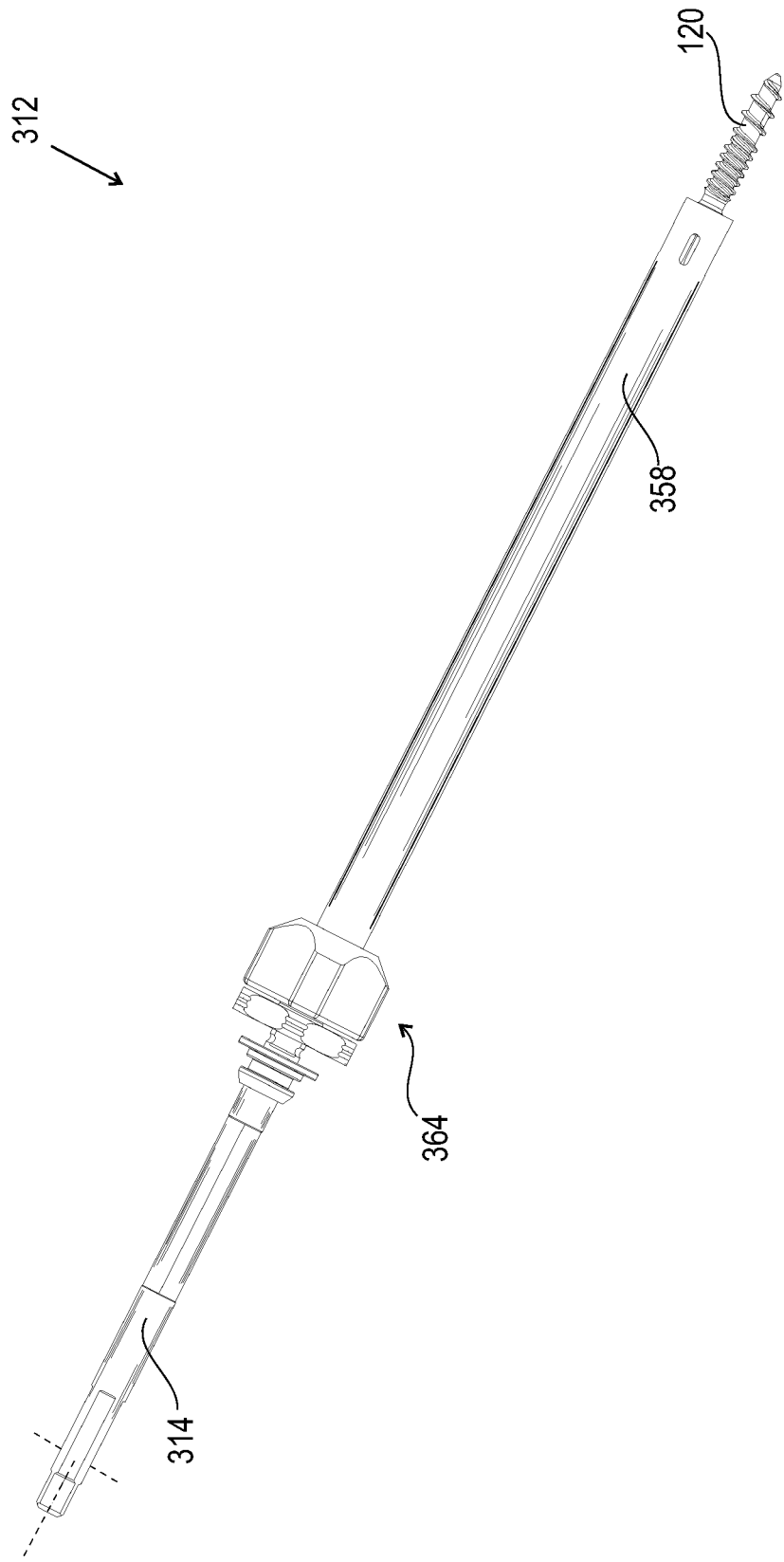
FIG. 23 is a perspective view of components of one embodiment of a surgical system in accordance with the principles of the present disclosure.

A navigation component 202 engages section 20 of shaft 14 and is oriented relative to a sensor array 204, as shown in FIG. 22, to facilitate communication between navigation component 202 and sensor array 204 during a surgical procedure, as described herein. Navigation component 202 is configured to generate a signal representative of a position of bone fastener 120 relative to surgical driver 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 202 includes an emitter array 206. Emitter array 206 is configured for generating a signal to sensor array 204 of a surgical navigation system 208. In some embodiments, the signal generated by emitter array 206 represents a position of bone fastener 120 relative to surgical driver 12 and relative to tissue, for example, bone. In some embodiments, the signal generated by emitter array 206 represents a three-dimensional position of bone fastener 120 relative to tissue. In some embodiments, emitter array 206 may include passive/reflective markers. In some embodiments, emitter array 206 can be attached to a camera.

In some embodiments, sensor array 204 receives signals from emitter array 206 to provide a three-dimensional spatial position and/or a trajectory of bone fastener 120 relative to surgical driver 12 and/or tissue. Emitter array 206 communicates with a processor of a computer 210 of surgical navigation system 208 to generate data for display of an image on a monitor 212, as described herein. In some embodiments, sensor array 204 receives signals from emitter array 206 to provide a visual representation of a position of bone fastener 120 relative to surgical driver 12 and/or tissue. See, for example, similar surgical navigation components and their use as described in U.S. Pat. Nos. 6,021,343, 6,725,080, and 6,796,988, the entire contents of each of these references being incorporated by reference herein.

Surgical navigation system 208 is configured for acquiring and displaying medical imaging, for example, x-ray images appropriate for a given surgical procedure. In some embodiments, pre-acquired images of a patient are collected. In some embodiments, surgical navigation system 208 can include an O-Arm® imaging device 214 sold by Medtronic Navigation, Inc. having a place of business in Louisville, Colo., USA. Imaging device 214 may have a generally annular gantry housing that encloses an image capturing portion 216.

In some embodiments, image capturing portion 216 may include an x-ray source or emission portion and an x-ray receiving or image receiving portion located generally or as practically possible 180 degrees from each other and mounted on a rotor (not shown) relative to a track of image capturing portion 216. Image capturing portion 216 can be operable to rotate 360 degrees during image acquisition. Image capturing portion 216 may rotate around a central point or axis, allowing image data of the patient to be acquired from multiple directions or in multiple planes. Surgical navigation system 208 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 208 can include C-arm fluoroscopic imaging systems, which can generate three-dimensional views of a patient. The position of image capturing portion 216 can be precisely known relative to any other portion of an imaging device of surgical navigation system 208. In some embodiments, a precise knowledge of the position of image capturing portion 216 can be used in conjunction with a tracking system 218 to determine the position of image capturing portion 216 and the image data relative to the patient.

Tracking system 218 can include various portions that are associated or included with surgical navigation system 208. In some embodiments, tracking system 218 can also include a plurality of types of tracking systems, for example, an optical tracking system that includes an optical localizer, for example, sensor array 204 and/or an EM tracking system that can include an EM localizer. Various tracking devices can be tracked with tracking system 218 and the information can be used by surgical navigation system 208 to allow for a display of a position of an item, for example, a patient tracking device, an imaging tracking device 220, and an instrument tracking device, for example, emitter array 206, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, and 5,592,939, the entire contents of each of these references being incorporated by reference herein.

Fluoroscopic images taken are transmitted to a computer 222 where they may be forwarded to computer 210. Image transfer may be performed over a standard video connection or a digital link including wired and wireless. Computer 210 provides the ability to display, via monitor 212, as well as save, digitally manipulate, or print a hard copy of the received images. In some embodiments, images may also be displayed to the surgeon through a heads-up display.

In some embodiments, surgical navigation system 208 provides for real-time tracking of the position of bone fastener 120 relative to surgical driver 12 and/or tissue can be tracked. Sensor array 204 is located in such a manner to provide a clear line of sight with emitter array 206, as described herein. In some embodiments, fiducial markers of emitter array 206 communicate with sensor array 204 via infrared technology. Sensor array 204 is coupled to computer 210, which may be programmed with software modules that analyze signals transmitted by sensor array 204 to determine the position of each object in a detector space.

Surgical driver 12 is configured for use with a guide member, for example, an end effector 200 of robotic arm R. End effector 200 is configured for passage of bone fastener 120 and disposal of surgical driver 12. Robotic arm R includes position sensors (not shown), similar to those referenced herein, which measure, sample, capture and/or identify positional data points of end effector 200 in three-dimensional space for a guide-wireless insertion of bone fasteners 120 with tissue. In some embodiments, the position sensors of robotic arm R are employed in connection with surgical navigation system 208 to measure, sample, capture and/or identify positional data points of end effector 200 in connection with surgical treatment, as described herein. The position sensors are mounted with robotic arm R and calibrated to measure positional data points of end effector 200 in three-dimensional space, which are communicated to computer 210.

Shaft 14 is aligned with mating surface 122 of bone fastener 120. Collet 52 via sleeve 58 snap fits around head 124 to provisionally capture head 124. Actuator 24 via lever 84, causes translation of sleeve 58 in the direction of arrow E shown in FIG. 5, such that end 62 of sleeve 58 translates over collet 52 to position collet 52 in the contractable orientation. Lever 84 rotates via pivot point 86 in the direction of arrow B shown in FIG. 5, causing pivot point 86 to be rotatable past axial alignment/top dead center to fix the position of shaft 14 with bone fastener 120, positioning levers 82, 84 in the locked orientation, as described herein. The position of shaft 14 is fixed with bone fastener 120 to prevent undesirable loosening, toggle, offset and/or, connection and misalignment of bone fastener 120 with surgical driver 12.

Navigation component 202 is oriented relative to sensor array 204, to facilitate communication between navigation component 202 and sensor array 204 during the surgical procedure. This configuration provides indicia or display from surgical navigation system 208, as described herein, of components of spinal implant system 10, including bone fastener 120 and surgical driver 12, and their relative positions with tissue in connection with the surgical treatment. Surgical driver 12 is inserted through end effector 200 for insertion to the surgical site.

Bone fastener 120 is implanted at the surgical site and surgical driver 12 is disengaged from bone fastener 120. To disengage surgical driver 12 from bone fastener 120, lever 82 is rotated in the opposite direction, shown by arrow A in FIG. 5 which causes translation of sleeve 58 in the direction shown by arrow F in FIG. 5, such that end 62 of sleeve 58 translates away from collet 52 to position collet 52 in the expandable orientation. Lever 82 rotates via pivot point 86 in the direction shown by arrow A in FIG. 5, causing pivot point 86 to be axially aligned to position levers 82, 84 in the non-locked orientation, disengaging shaft 14 with bone fastener 120. Surgical driver 12 is removed from the surgical site.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, surgical driver 12 is guided to the surgical site via a guidewire, for example, a K-wire (not shown) and/or without the use of an image guide, as described herein.

In one embodiment, as shown in FIGS. 23-33, spinal implant system 10, similar to the systems and methods described herein, includes surgical driver 312, similar to surgical driver 12. Surgical driver 312 is configured to engage, capture and/or interface with a spinal implant, for example, bone fastener 120, and is configured to prevent undesirable loosening, toggle, offset and/or, connection and misalignment of bone fastener 120 with surgical driver 312, as described herein.

Surgical driver 312 includes a driver 314, similar to driver shaft 14, described herein, extending along a longitudinal axis BB between a proximal end 316 and a distal end 318, as shown FIG. 24. End 316 is configured for engagement with a surgical tool. End 318 is configured for engagement with an implant, for example, bone fastener 120. End 318 includes a mating surface 320, similar to mating surface 38, described herein, configured for engagement with mating surface 122 of bone fastener 120. In some embodiments, ends 316, 318 may have various surface configurations, including, smooth, rough, arcuate, undulating, porous, semi-porous, dimpled, polished and/or textured.

Surgical driver 312 includes a sleeve 340, similar to sleeve 40, described herein, configured for disposal of a portion of driver 314, as shown in FIGS. 26 and 27. Sleeve 340 extends between a threaded end 342 and an end 344 along axis BB. End 342 is configured for engagement with a portion of driver 314 via a tab 346 of driver 314 that is configured for disposal within a slot 348 of sleeve 340, shown in FIGS. 25 and 27. End 344 includes an expandable portion, for example, a collet 352, similar to collet 52, described herein. Collet 352 is configured for movement between an expandable configuration and a contractable configuration, described herein. Collet 352 is configured for engagement with surfaces of head 124 of bone fastener 120.

Driver 314 axially translates relative to collet 352 and is limited to avoid mis-assembly of bone fastener 120 and ensures that mating surface 320 is fully engaged into bone fastener 120 when collet 352 is engaged. A sleeve 358, described herein, will not cover collet 352 unless mating surface 320 is fully engaged with bone fastener 120 to prevent mis-assembly by the user.

Surgical driver 312 includes sleeve 358, similar to sleeve 58, described herein. Sleeve 358 is configured for engagement with collet 352 to releasably capture bone fastener 120. Sleeve 358 extends between a proximal end 360 and a distal end 362 along axis BB. End 360 is configured for engagement with threaded end 342 of sleeve 340 via an inner threaded surface (not shown), and a portion of an actuator 364, described herein. End 362 is configured for engagement with collet 352 such that translation of sleeve 358 in a distal direction causes end 362 to slide over collet 352 to move collet between the expandable configuration to the contractable configuration around head 124 of bone fastener 120 to lock collet 352 with head 124.

Actuator 364 is configured for connection with sleeve 340 and sleeve 358 such that sleeve 358 is axially translatable relative to the sleeve 340 between a non-locked orientation (FIG. 28) and a locked orientation (FIG. 29) to fix position of driver 314 relative to head 124 and to prevent release of bone fastener 120. In the locked orientation, bone fastener 120 is prevented from loosening and toggle. Actuator 364 includes a ratchet, for example, a clutch 366, shown in FIG. 33. In some embodiments, clutch 366 includes a roller clutch, spring clutch, overrunning clutch, or one-way clutch.

Clutch 366 is configured for disposal within a knob 368 and engagement with sleeve 340 and sleeve 358. Clutch 366 is rotatable about axis BB in a first direction, for example, a clockwise direction, shown by arrow G in FIG. 28 and is prevented from rotation about axis BB in a second opposite direction, for example, a counterclockwise direction, shown by arrow H in FIG. 28. For example, clutch 366 includes one or more rollers 370 disposed within a wedge shaped slot or cam configuration such that when clutch 366 is rotated with actuator 364/knob 368 in the clockwise direction, rollers 370 function as roller bearings and facilitate rotation of clutch 366 about axis BB. When clutch 366 is rotated in the counterclockwise direction, the wedge shaped slot or cam configuration cause rollers 370 to become wedged or fixed and prevents rotation of clutch 366 about axis BB. In some embodiments, clutch 366 includes eight rollers 370. In some embodiments, clutch 366 is manufactured as a metal clutch 366 (see, for example, a similar clutch design Stainless One-Way Clutch Bearing, S-HF1008, Boca Bearing Company, Boynton Beach, FL, USA). In some embodiment, clutch 366 is press fit or welded to knob 368.

Clutch 366 is configured to prevent accidental loosening and off-axis alignment of bone fastener 120. For example, clutch 366 is rotatable about axis BB in the first direction to axially translate sleeve 358 into the locked orientation to fix position of driver 314 relative to head 124 and to prevent release of bone fastener 120. As sleeve 358 axially translates, rotation of clutch 366 incrementally tightens surgical driver 312 with bone fastener 120. In some embodiments, clutch 366 provides a continuous and/or infinitesimal rotational lock, for example, including selected angular orientations. In some embodiments, the selected angular orientation can include an angular increment selected from a range of greater than 0 through 20 degrees. In some embodiments, the selected angular increment can include about 2, 3, or 4 angular degrees.

Figure 29:
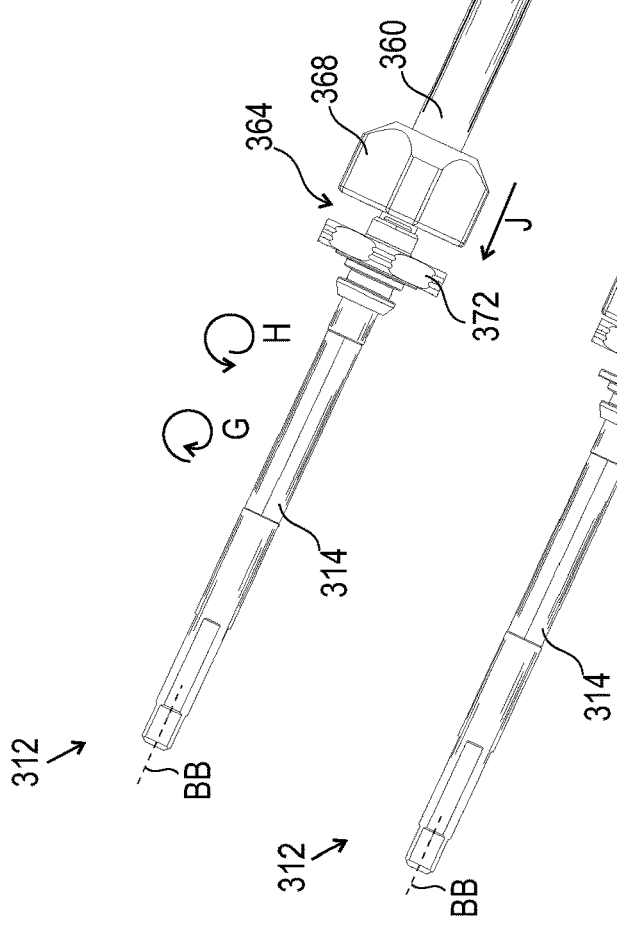
FIG. 29 is a perspective view of the components shown in FIG. 23.
Figure 32:
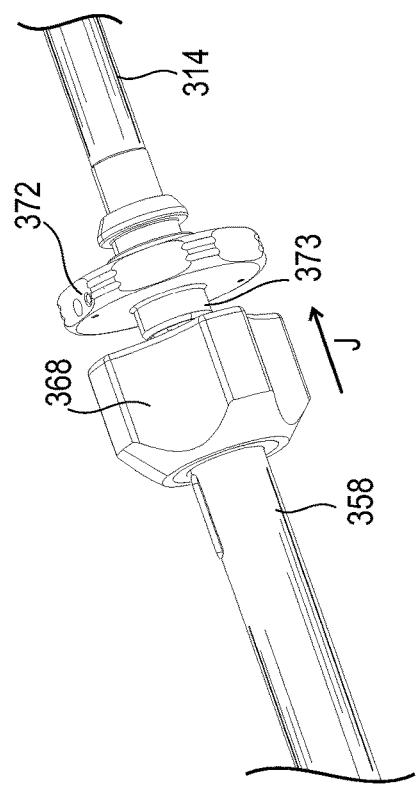
FIG. 32 is a break away view of components shown in FIG. 23.
Figure 34:
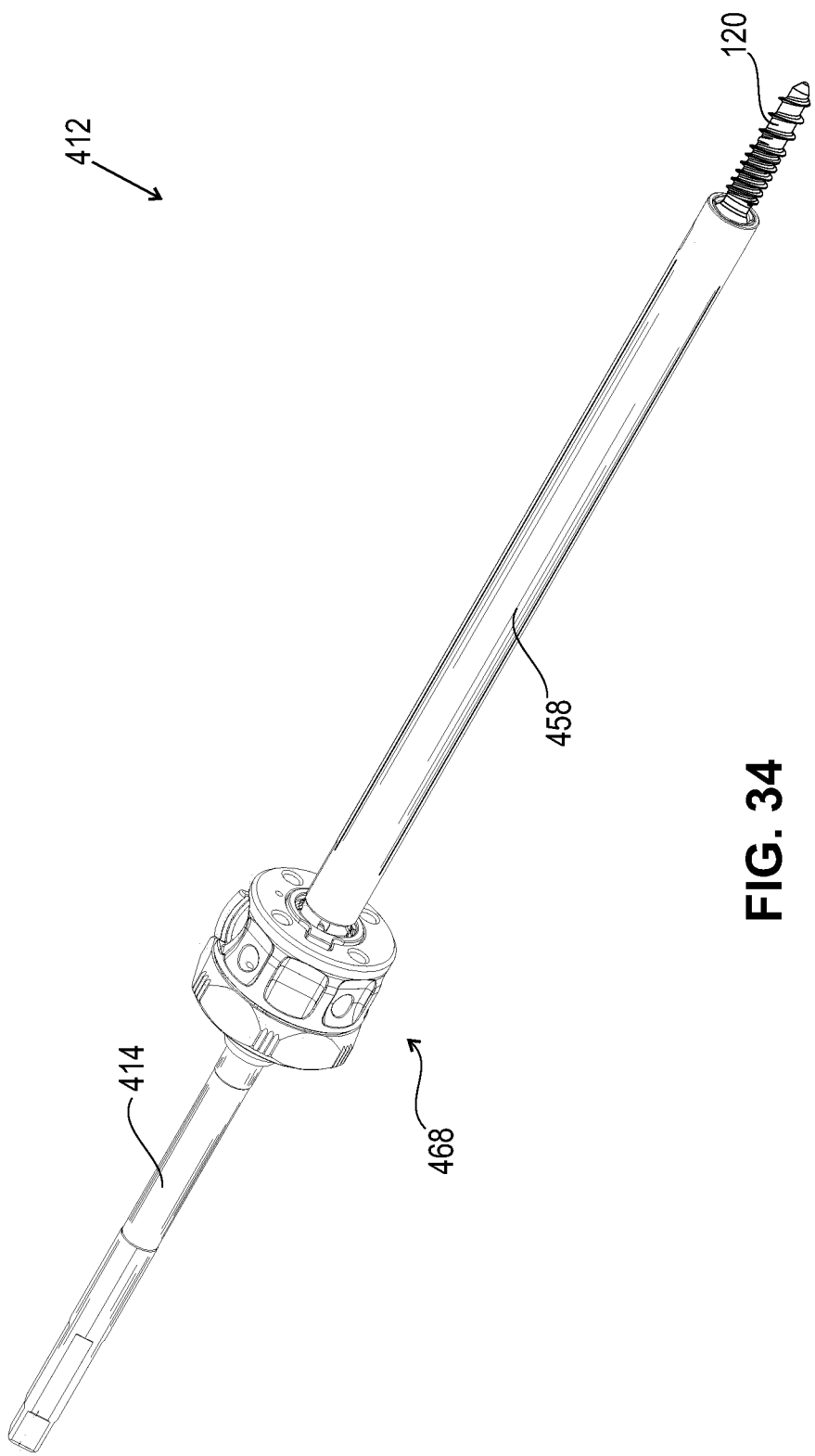
FIG. 34 is a perspective view of components of one embodiment of a surgical system in accordance with the principles of the present disclosure.

Actuator 364 includes a lock, for example, a slider lock 372 including a hub 373, shown in FIG. 32, configured for engagement with clutch 366, shown in FIG. 29. Slider lock 372 via hub 373 is configured to engage clutch 366 via rollers 370 to lock clutch 366, thus preventing rotation of clutch 366. Slider lock 372 is configured to disengage with clutch 366 to allow rotation of clutch 366. Slider lock 372 includes ball detent mechanisms 374, 376 shown in FIG. 30, configured to lock slider lock 372 in a locked or unlocked state. To lock clutch 366 via slider lock 372, slider lock 372 is translated in a direction, shown by arrow I in FIG. 29, to engage and lock clutch 366. To unlock and disengage with clutch 366, slider lock 372 is translated in an opposite direction, shown by arrow J in FIG. 28. In some embodiments, when clutch 366 is locked, a surgeon can place their hand on knob 368 or sleeve 358 without risking accidental loosening of clutch 366.

Actuator 364, including clutch 366 is prevented from rotation in the second direction to resist and/or prevent movement of sleeve 358 relative to sleeve 340. In some embodiments, actuator 364 including clutch 366 is prevented from rotation in the second direction within a selected angle in a range of variational tolerance of 1 through 5 angular degrees.

In assembly, operation and use, spinal implant system 10 including surgical driver 312, similar to the systems and methods described herein, is employed with a surgical procedure, for example, a treatment of an applicable condition or injury of an affected section of a spinal column and adjacent areas within a body. For example, to place surgical driver 312 in the locked orientation which locks bone fastener 120 to surgical driver 312, mating surface 122 of bone fastener 120 engages with mating surface 320 of driver 314. Sleeve 358 is translated in a direction, shown by arrow K in FIG. 28 via rotation of knob 368 and clutch 366 in the first direction shown by arrow G in FIG. 28. End 362 of sleeve 358 engages with collet 352 to move into the contractable configuration around head 124 of bone fastener 120 to position surgical driver 312 in the locked orientation. Rotation of clutch 366 incrementally tightens surgical driver 312 with bone fastener 120 and prevents release of bone fastener 120. In the locked orientation, bone fastener 120 is prevented from loosening and toggle. Clutch 366 is locked via slider lock 372, by translating slider lock 372 in the direction shown by arrow I in FIG. 29 to engage clutch 366 with slider lock 372.

Figure 28:
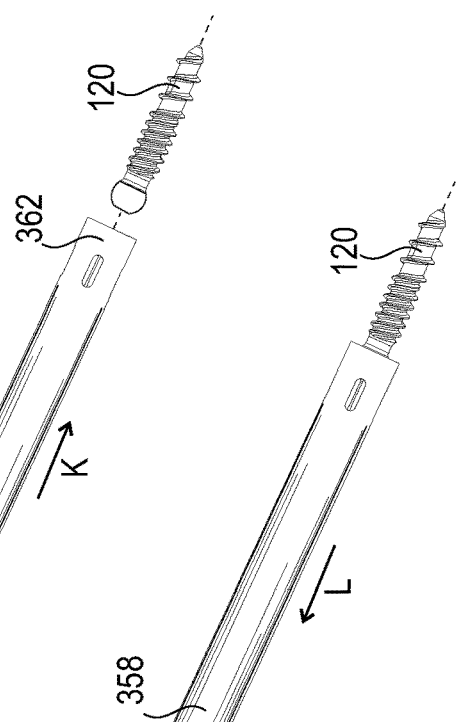
FIG. 28 is a perspective view of the components shown in FIG. 23.
Figure 31:
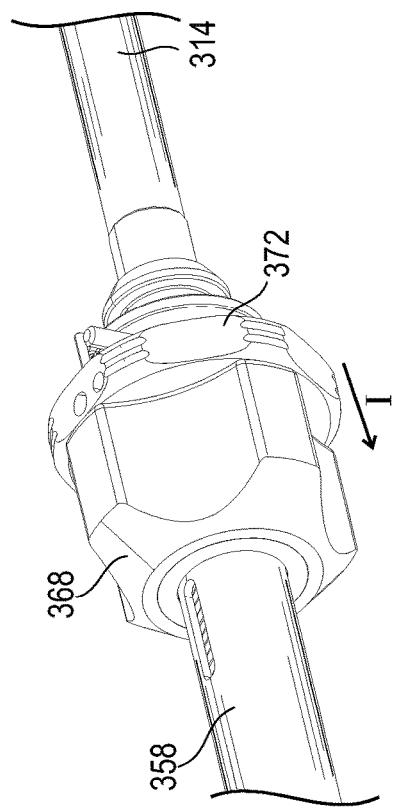
FIG. 31 is a break away view of components shown in FIG. 23.
Figure 33:
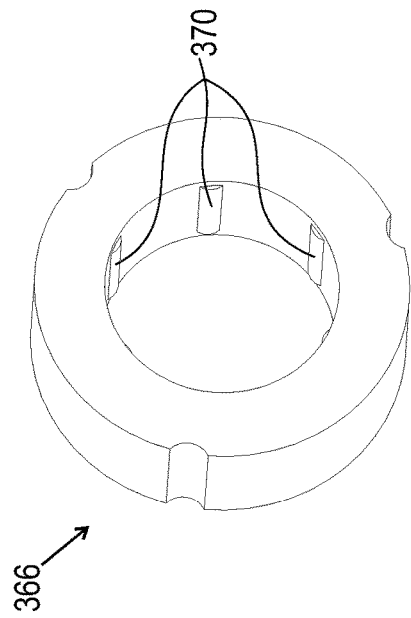
FIG. 33 is a break away view of components shown in FIG. 23.
Figure 30:
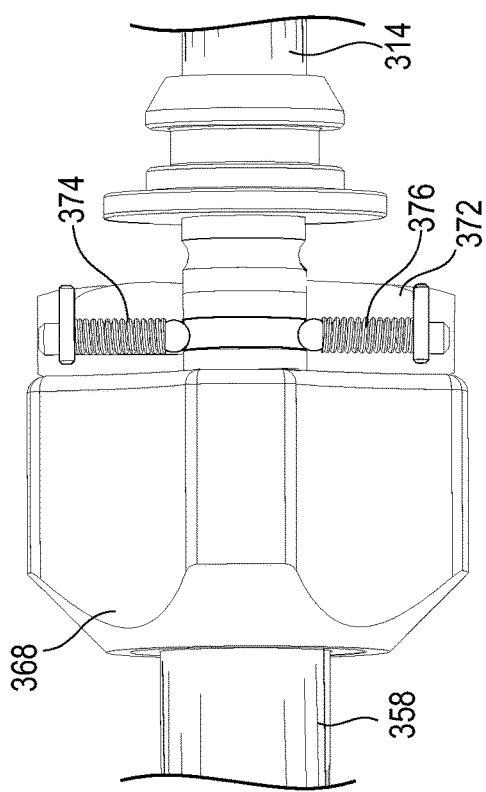
FIG. 30 is a break away in part phantom view of components shown in FIG. 23.

To place surgical driver 312 in the non-locked orientation which releases bone fastener 120 from surgical driver 312, clutch 366 is unlocked via slider lock 372, by translating slider lock 372 in the direction shown by arrow J in FIG. 28 to disengage clutch 366 from slider lock 372. Sleeve 358 is translated in a direction, shown by arrow L in FIG. 29 via rotation of knob 368 to position surgical driver 312 in the non-locked orientation to release bone fastener 120. In some embodiments, navigation, as described herein, can be implemented with surgical driver 312.

In one embodiment, as shown in FIGS. 34-81, spinal implant system 10, similar to the systems and methods described herein, includes surgical driver 412, similar to surgical driver 312. Surgical driver 412 is configured to engage, capture and/or interface with a spinal implant, for example, bone fastener 120, and is configured to prevent undesirable loosening, toggle, offset and/or, connection and misalignment of bone fastener 120 with surgical driver 412, as described herein.

Figure 35:
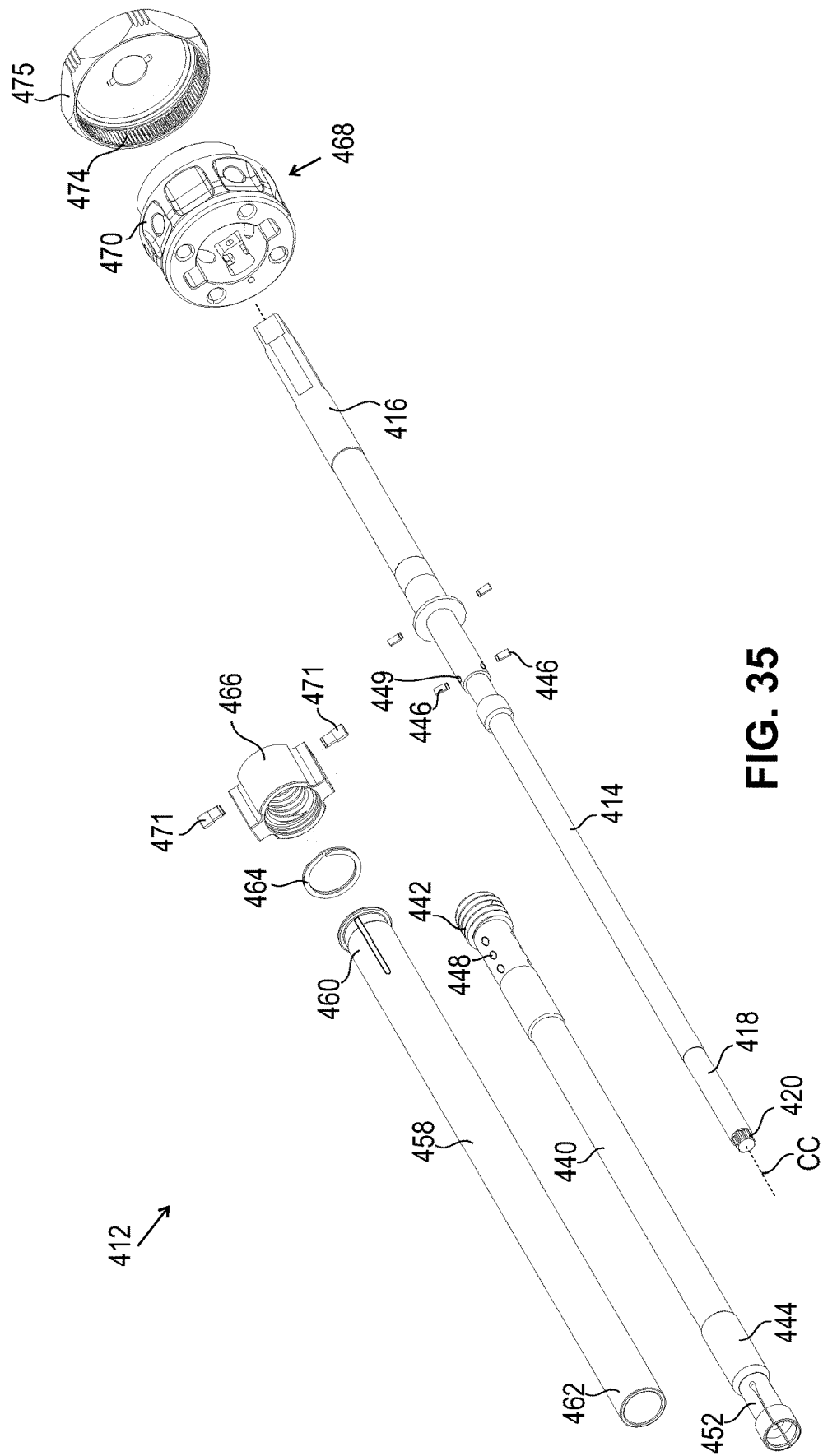
FIG. 35 is a perspective view of the components shown in FIG. 34 with parts separated.
Figure 37:
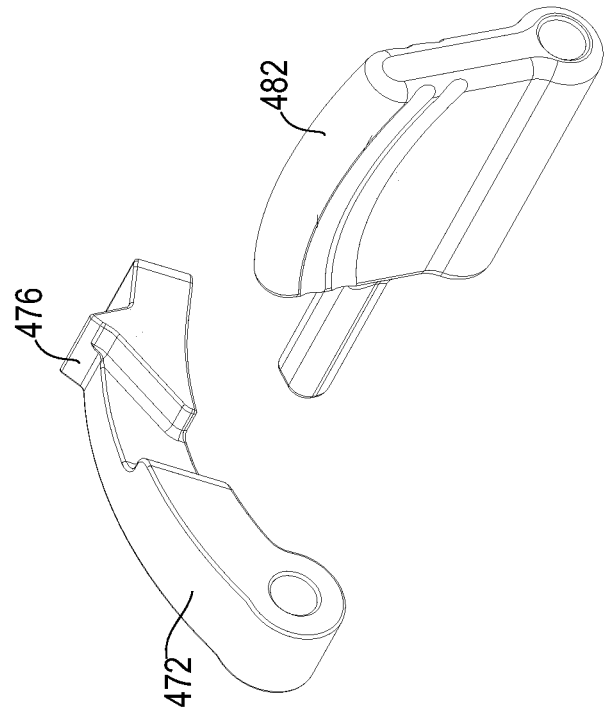
FIG. 37 is a perspective view of components shown in FIG. 36 with parts separated.
Figure 36:
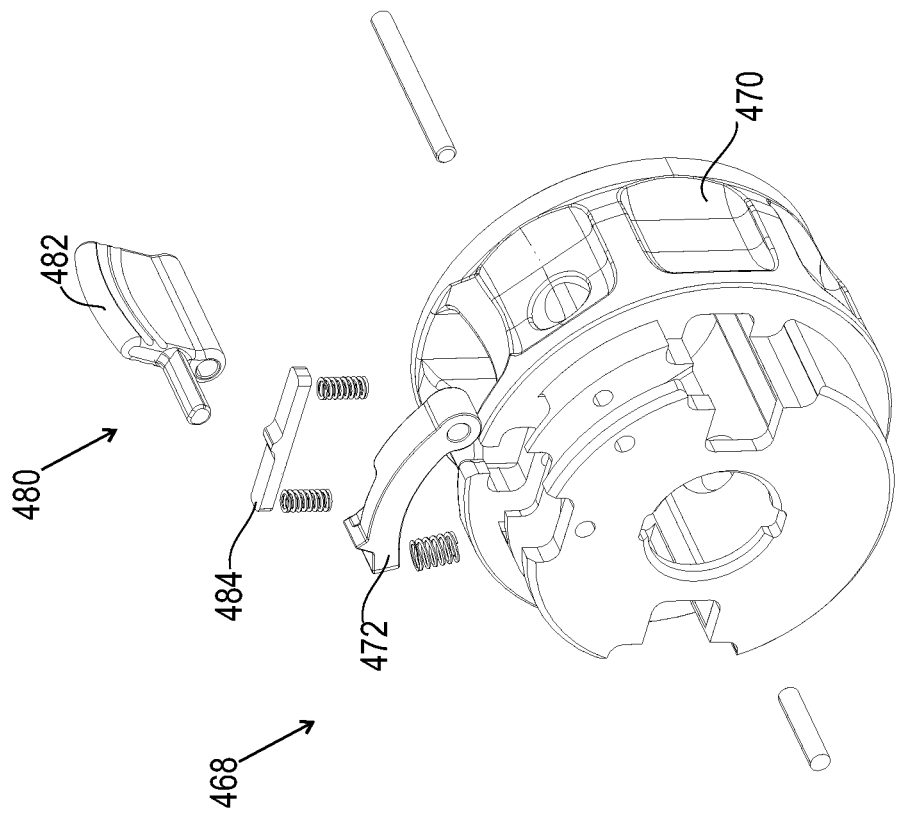
FIG. 36 is a perspective view of the components shown in FIG. 34 with parts separated.
Figure 41:
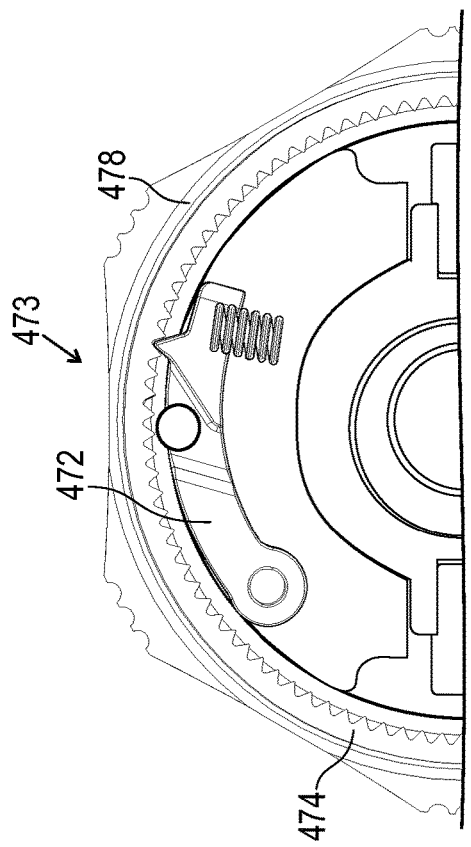
FIG. 41 is a break away cross section view of components shown in FIG. 40.
Figure 40:
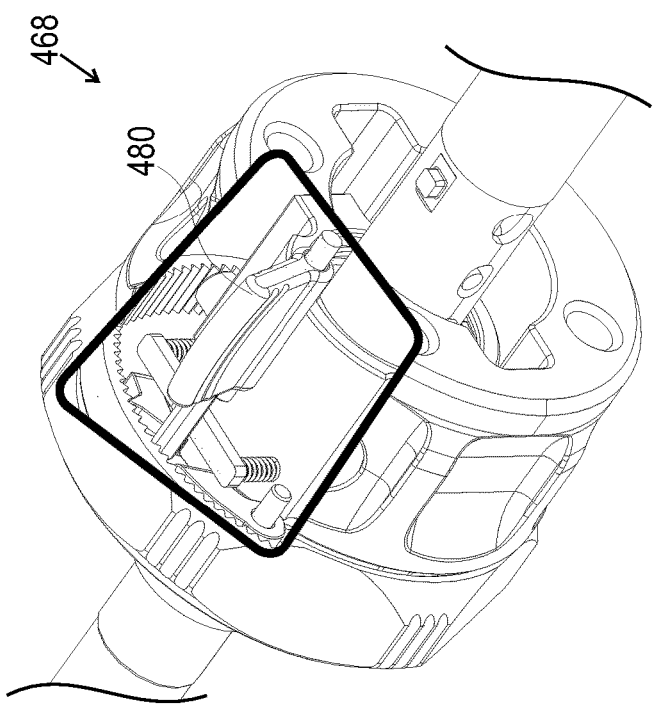
FIG. 40 is a break away in part cutaway view of components shown in FIG. 34.
Figure 43:
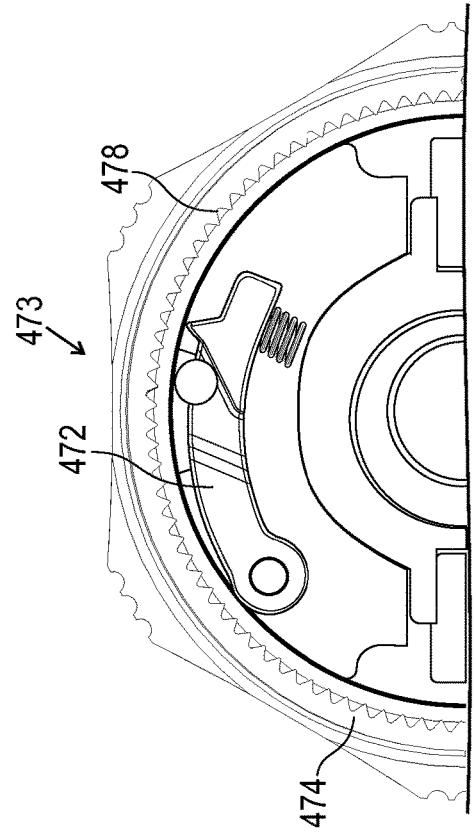
FIG. 43 is a break away cross section view of components shown in FIG. 42.
Figure 42:
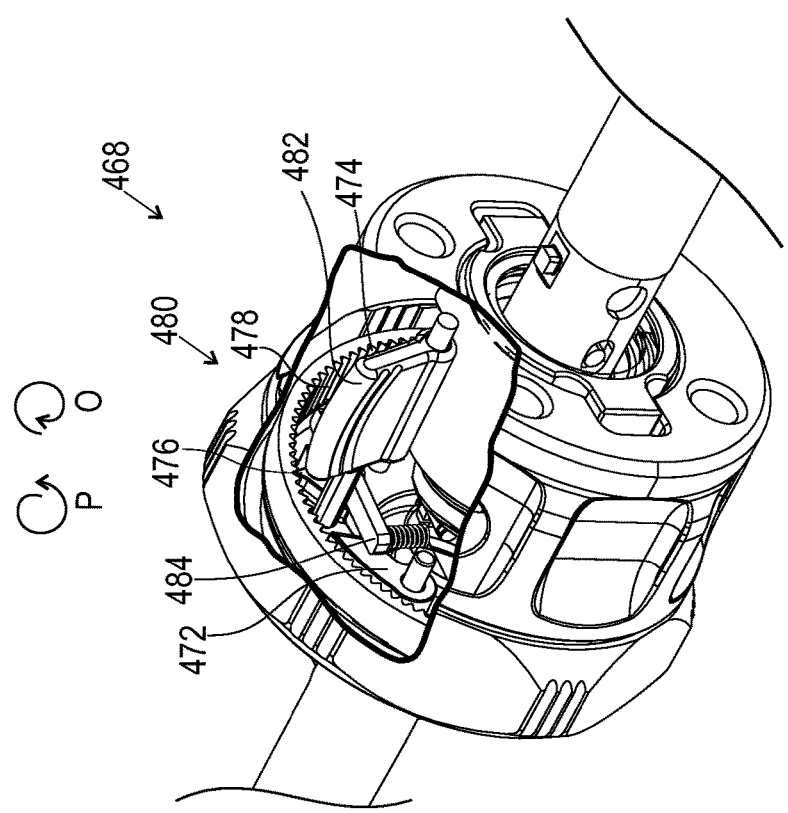
FIG. 42 is a break away in part cutaway view of components shown in FIG. 34.
Figure 49:
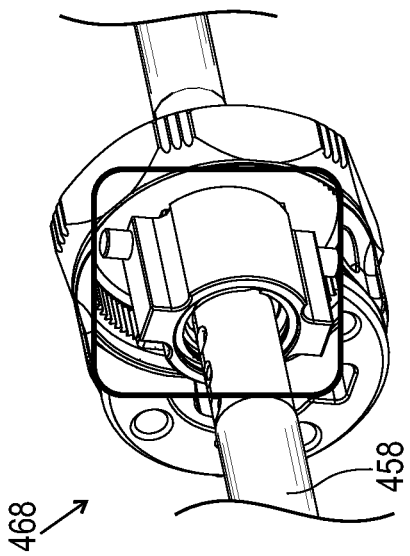
FIG. 49 is a break away in part cutaway view of components shown in FIG. 34.
Figure 48:
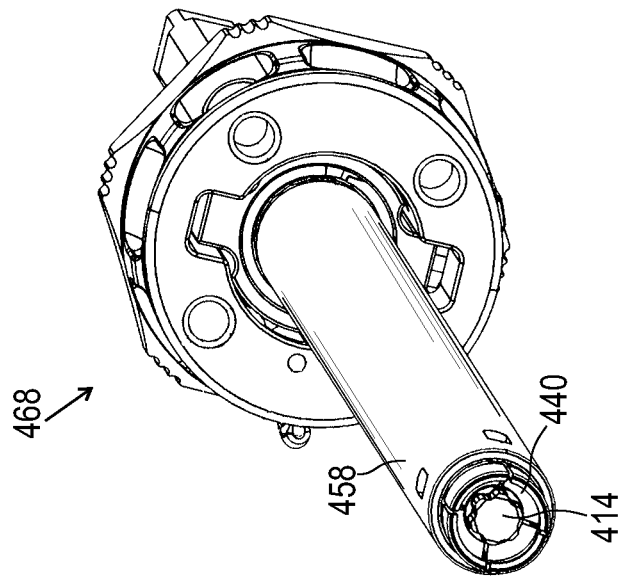
FIG. 48 is a break away view of components shown in FIG. 34.
Figure 50:
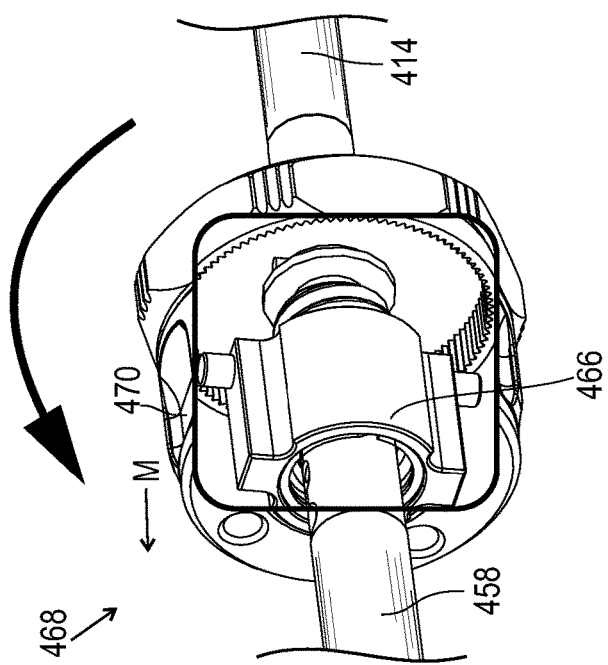
FIG. 50 is a break away in part cutaway view of components shown in FIG. 34.
Figure 51:
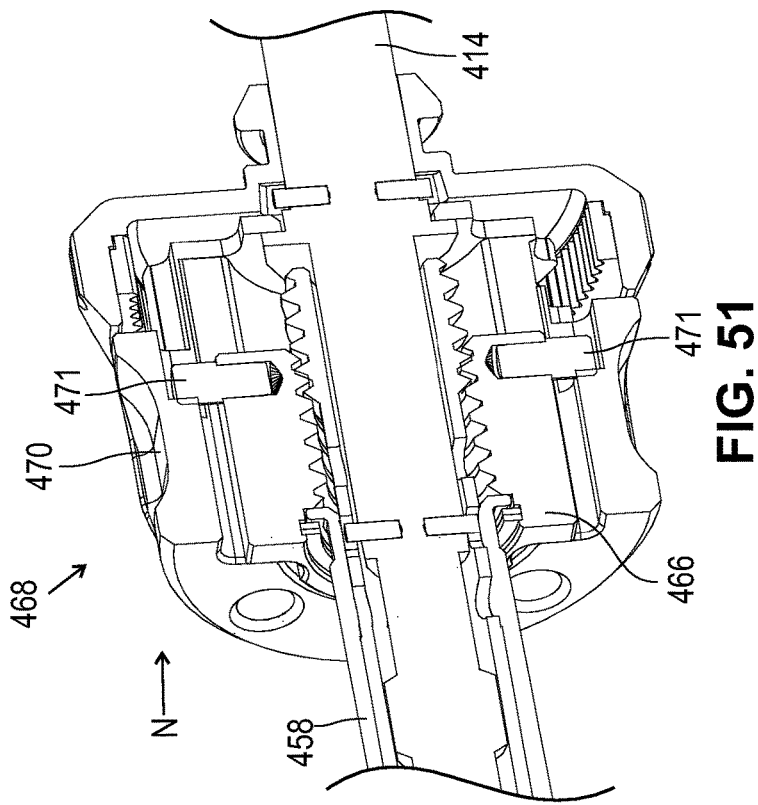
FIG. 51 is a break away cross section view of components shown in FIG. 34.
Figure 53:
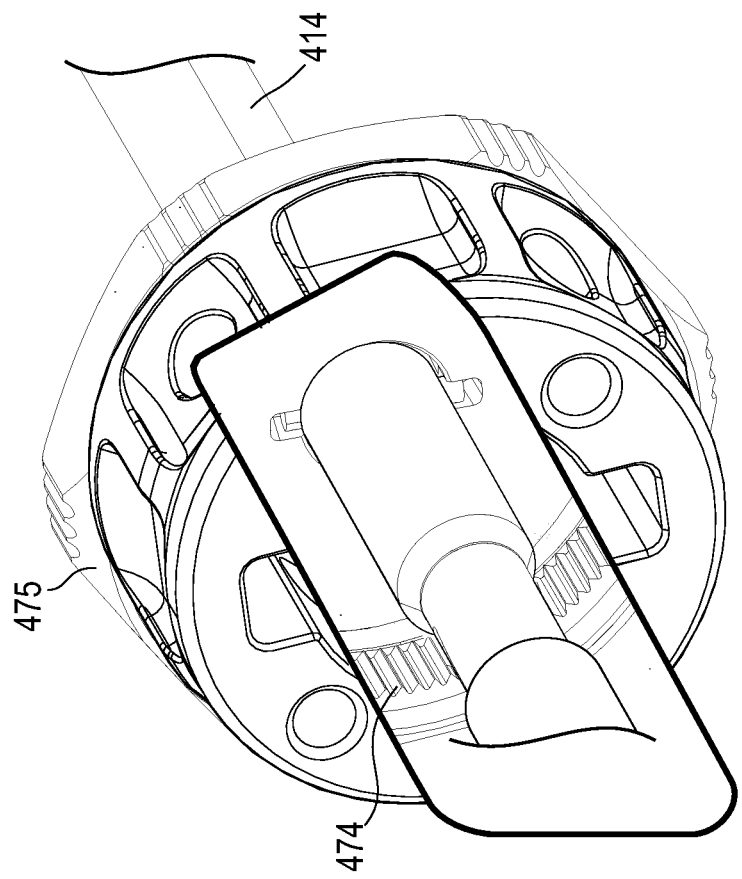
FIG. 53 is a break away in part cutaway view of components shown in FIG. 34.
Figure 52:
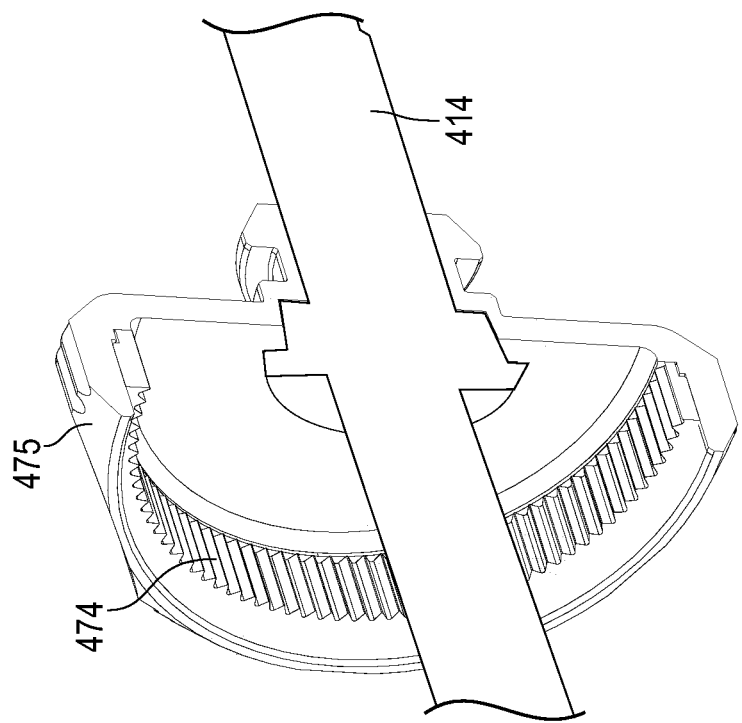
FIG. 52 is a break away cross section view of components shown in FIG. 34.
Figure 56:
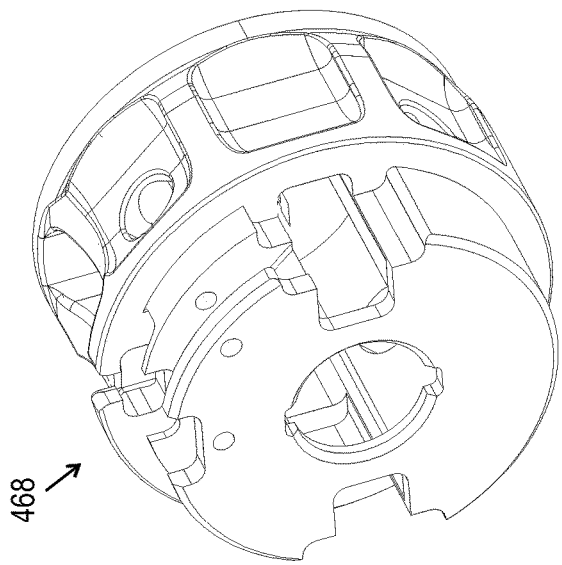
FIG. 56 is a break away view of components shown in FIG. 34.
Figure 55:
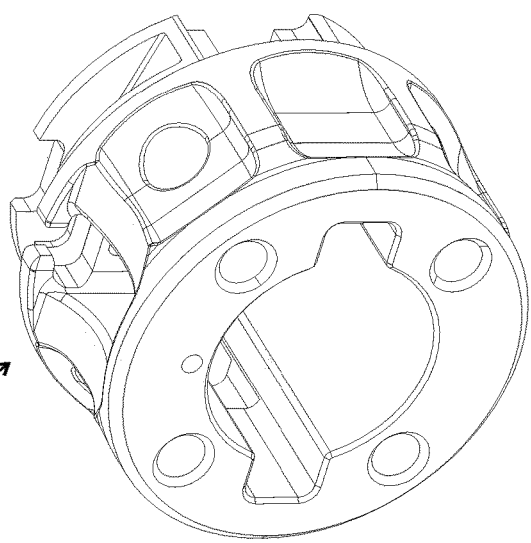
FIG. 55 is a break away view of components shown in FIG. 34.
Figure 54:
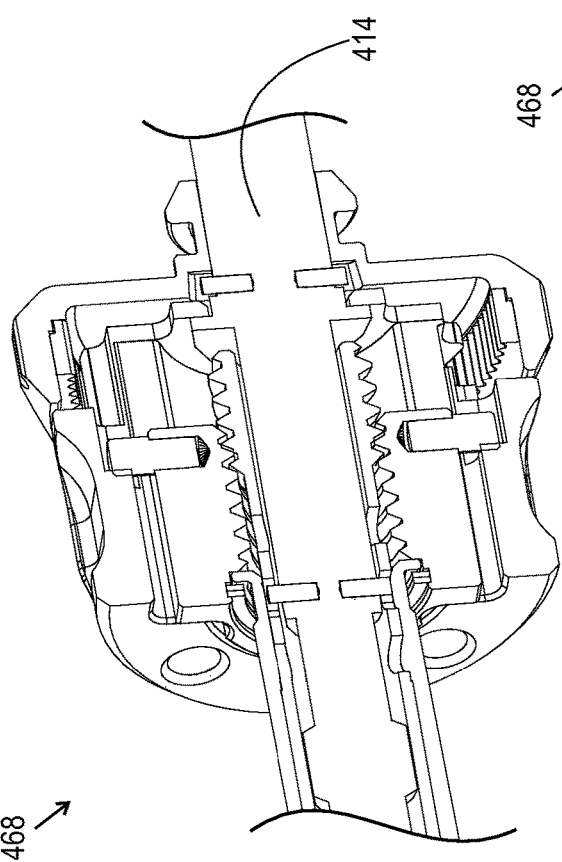
FIG. 54 is a break away cross section view of components shown in FIG. 34.
Figure 57:
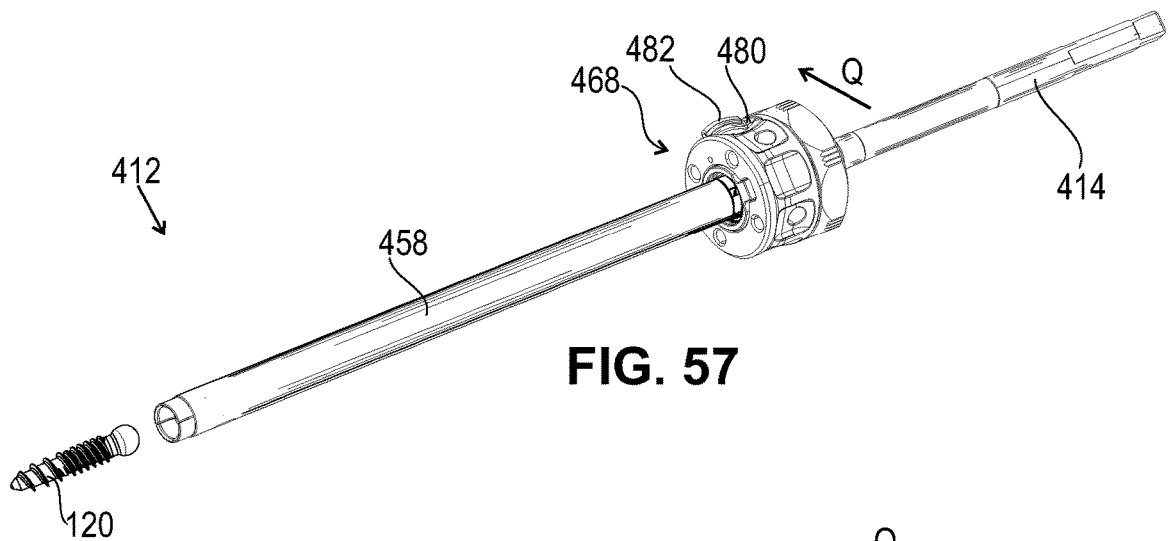
FIG. 57 is a perspective view of the components shown in FIG. 34.
Figure 58:
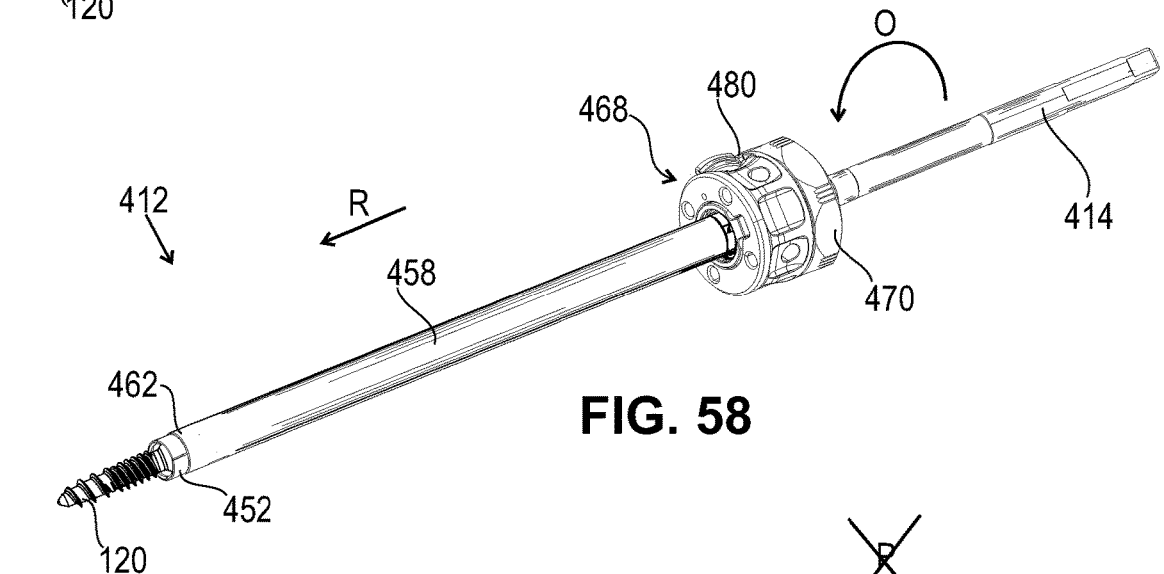
FIG. 58 is a perspective view of the components shown in FIG. 34.
Figure 59:
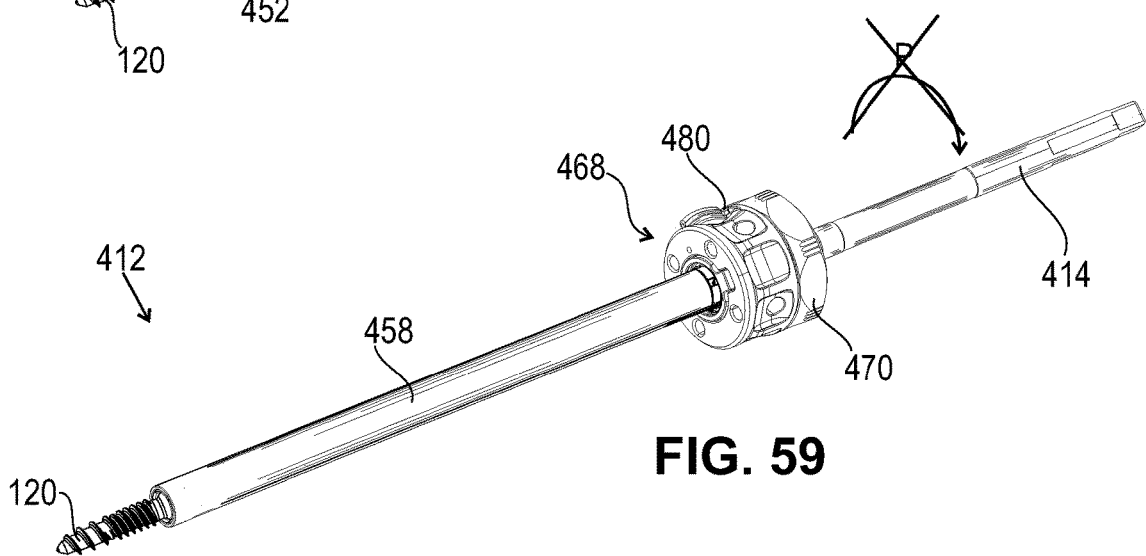
FIG. 59 is a perspective view of the components shown in FIG. 34.

Surgical driver 412 includes a driver 414, similar to driver 314, described herein, extending along a longitudinal axis CC between a proximal end 416 and a distal end 418, as shown FIG. 35. End 416 is configured for engagement with a surgical tool. End 418 is configured for engagement with an implant, for example, bone fastener 120. End 418 includes a mating surface 420, similar to mating surface 320, described herein, configured for engagement with mating surface 122 of bone fastener 120.

Surgical driver 412 includes a sleeve 440, similar to sleeve 340, described herein, configured for disposal of a portion of driver 414. Sleeve 440 extends between a threaded end 442 and an end 444 along axis CC. End 442 is configured for threaded engagement with an adjustment collar 466, described herein. End 442 is configured for engagement with a portion of driver 414 via pins 446 configured for disposal within opening 448 of sleeve 440 and opening 449 of driver 414, shown in FIGS. 35 and 67. Pins 446 are configured to secure mating surface 420 of shaft 414 within sleeve 440 and permits a finite amount of translation of shaft 414. The finite amount of translation of shaft 414 allows for tolerance variations during tensioning with bone fastener 120.

End 444 includes an expandable portion, for example, a collet 452, similar to collet 352, described herein. Collet 452 is configured for movement between an expandable configuration and a contractable configuration, described herein. Collet 452 is configured for engagement with surfaces of head 124 of bone fastener 120.

Driver 414 axially translates relative to collet 452 and is limited to avoid mis-assembly of bone fastener 120 and ensures that mating surface 420 is fully engaged into bone fastener 120 when collet 452 is engaged. A sleeve 458, described herein, will not cover collet 452 unless mating surface 420 is fully engaged with bone fastener 120 to prevent mis-assembly by the user.

Surgical driver 412 includes sleeve 458, similar to sleeve 358, described herein. Sleeve 458 is configured for engagement with collet 452 to releasably capture bone fastener 120. Sleeve 458 extends between a proximal end 460 and a distal end 462 along axis CC. End 460 is configured for engagement with a retaining ring 464 and adjustment collar 466, described herein. End 462 is configured for engagement with collet 452 such that translation of sleeve 458 in a distal direction causes end 462 to slide over collet 452 to move collet between the expandable configuration to the contractable configuration around head 124 of bone fastener 120 to lock collet 452 with head 124.

Surgical driver 412 includes an actuator 468 configured for connection with sleeve 440 and sleeve 458 such that sleeve 458 is axially translatable relative to the sleeve 440 between a non-locked orientation (FIGS. 57 and 62) and a locked orientation (FIG. 59) to fix position of driver 414 relative to head 124, and to prevent release of bone fastener 120. In the locked orientation, bone fastener 120 is prevented from loosening and toggle. Actuator 468 includes a knob 470, shown in FIG. 35. Knob 470 is configured for disposal of adjustment collar 466 such that adjustment collar 466 is rotationally fixed with knob 470 and translates axially in a direction, shown by arrow M in FIG. 50. Adjustment collar 466 rotates and translates axially in the direction of arrow M, and knob 470 rotates but does not translate axially. Adjustment collar 466 is prevented from axial translation in a direction, shown by arrow N in FIG. 51 via pins 471.

Actuator 468 includes a ratchet 473 configured to incrementally tighten surgical driver 412 with bone fastener 120. A portion of rachet 473, including a pawl 472 is configured for disposal within knob 470. Pawl 472 is configured for engagement with a ratchet ring 474 disposed within a bushing 475, shown in FIGS. 36-39. A tooth 476 of pawl 472 is engageable with ratchet ring 474 via a plurality of circumferential teeth 478 to facilitate rotation of actuator 468 about axis CC. A lock 480 including a lever 482 and a detent 484 is configured for engagement with pawl 472 such that ratchet 473 is rotated about axis CC in a first direction, for example, a clockwise direction shown by arrow P in FIG. 42 to incrementally tighten surgical driver 412 with bone fastener 120. Lock 480 is configured to prevent rotation of ratchet 473 about axis CC in a second direction, for example, a counterclockwise direction shown by arrow O in FIG. 42. In the second direction, actuator 468 is prevented from rotation to resist and/or prevent movement of sleeve 458 relative to sleeve 440. Lock 480 is oriented in a locked position which facilitates rotation of ratchet 473 in the first direction and prevents rotation of ratchet 473 in the second direction. Lock 480 is oriented in an unlocked position to facilitate free rotation of knob 470 and to disengage rachet 473.

In assembly, operation and use, spinal implant system 10 including surgical driver 412, similar to the systems and methods described herein, is employed with a surgical procedure, for example, a treatment of an applicable condition or injury of an affected section of a spinal column and adjacent areas within a body. For example, to place surgical driver 412 in the locked orientation which locks bone fastener 120 to surgical driver 412, lever 482 of lock 480 is translated in a direction, shown by arrow Q in FIG. 57 to orient lock 480 in the locked position to engage ratchet 473. Mating surface 122 of bone fastener 120 engages with mating surface 420 of driver 414. Sleeve 458 is translated in a direction, shown by arrow R in FIG. 58 via rotation of knob 470 and ratchet 473 in the first direction shown by arrow O. End 462 of sleeve 458 engages with collet 452 to move into the contractable configuration around head 124 of bone fastener 120 to position surgical driver 412 in the locked orientation. Rotation of ratchet 473 incrementally tightens surgical driver 412 with bone fastener 120. The locked position of lock 480 prevents rotation of ratchet 473 in the second direction shown by arrow P in FIG. 59.

Figure 60:
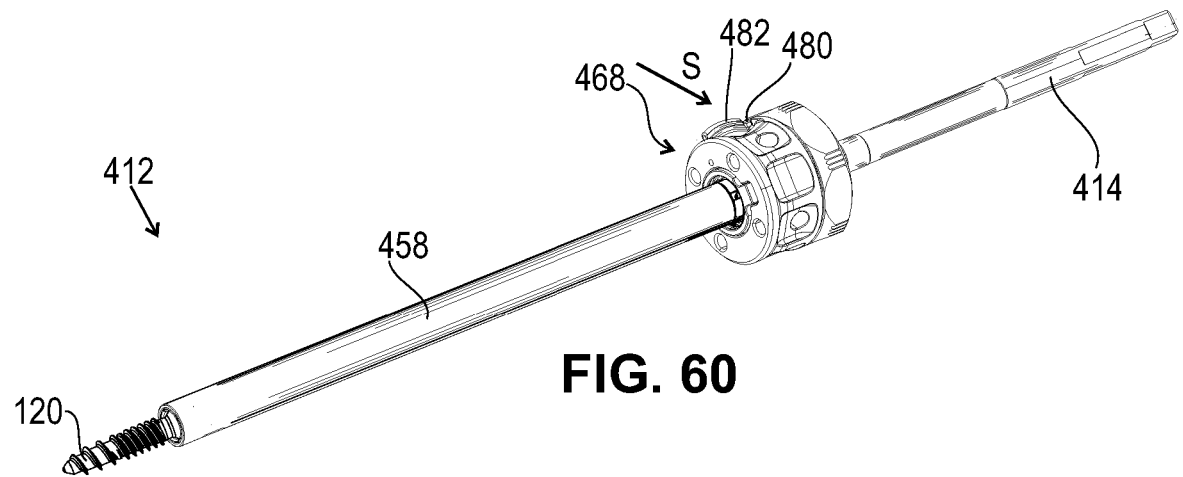
FIG. 60 is a perspective view of the components shown in FIG. 34.
Figure 61:
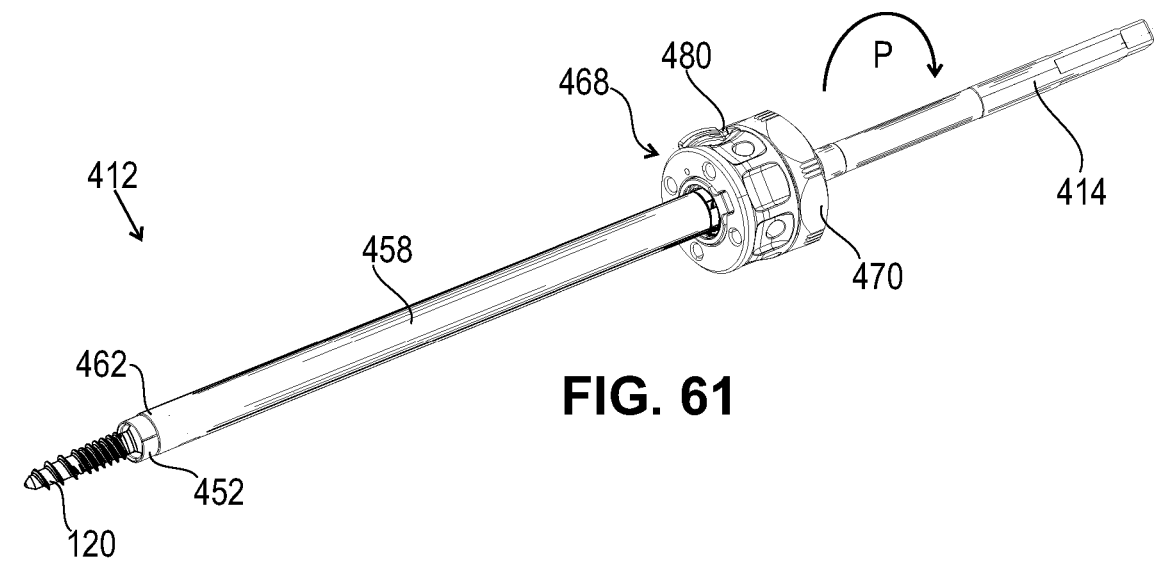
FIG. 61 is a perspective view of the components shown in FIG. 28.
Figure 62:
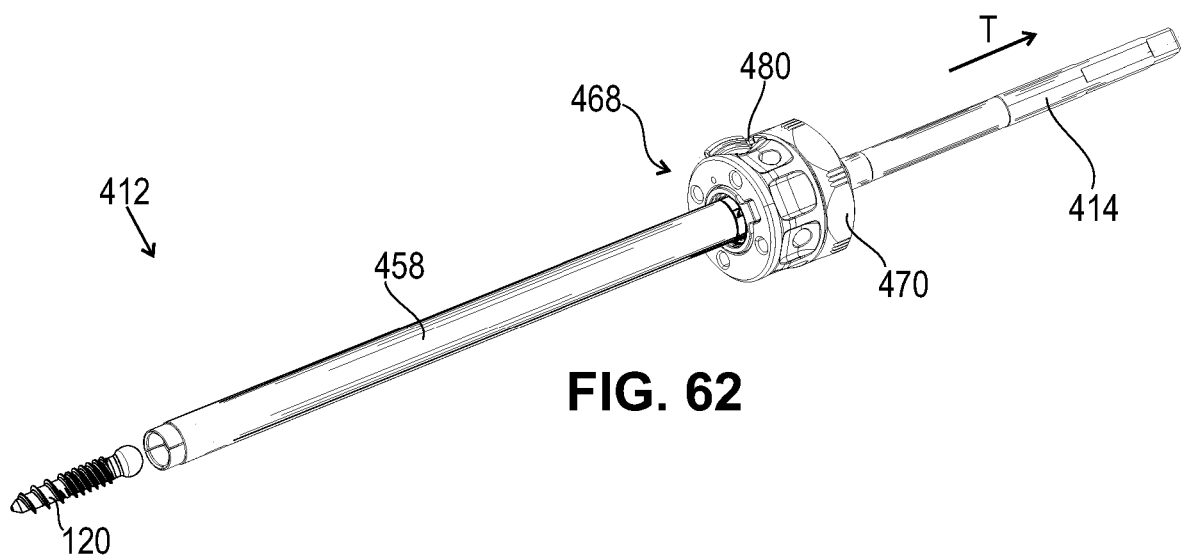
FIG. 62 is a perspective view of the components shown in FIG. 28.
Figure 63:
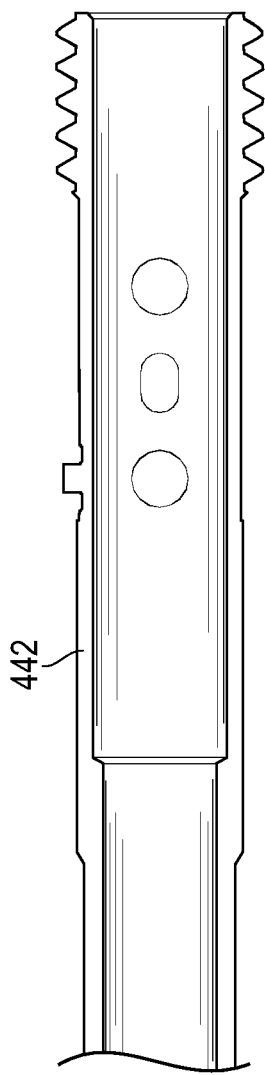
FIG. 63 is a break away view of components shown in FIG. 34.
Figure 64:
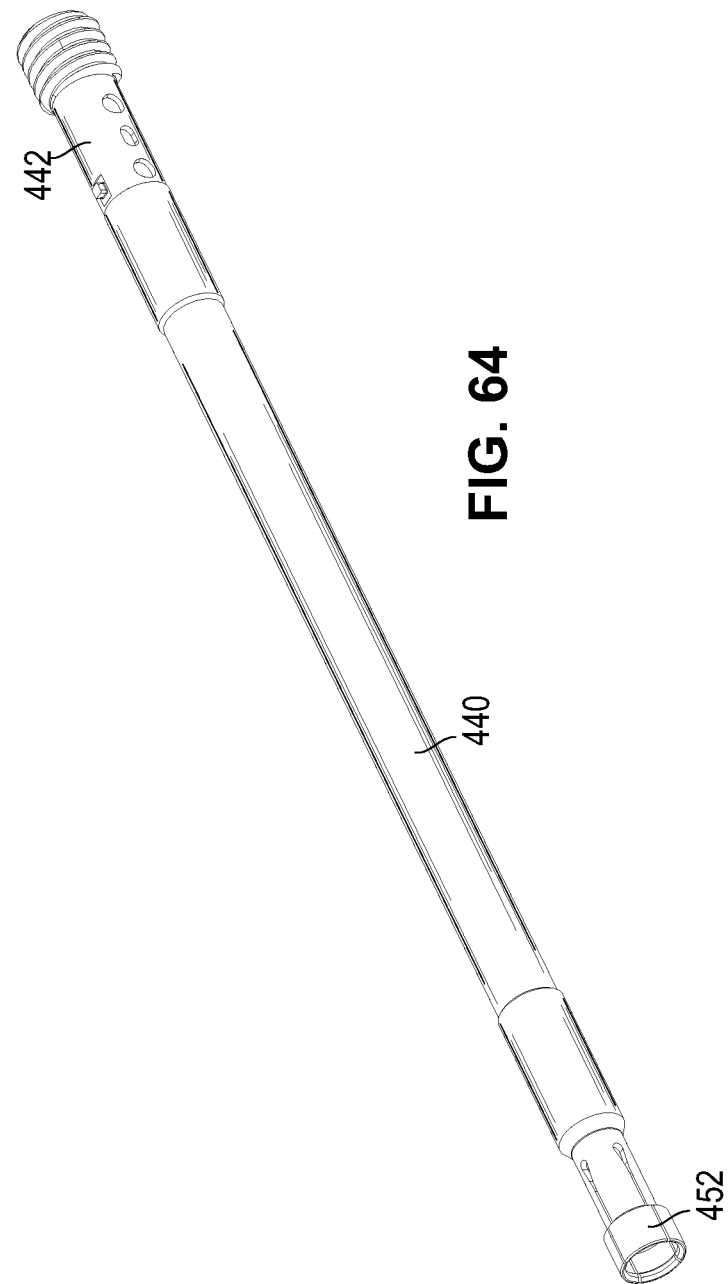
FIG. 64 is a perspective view of components shown in FIG. 34.
Figure 67:
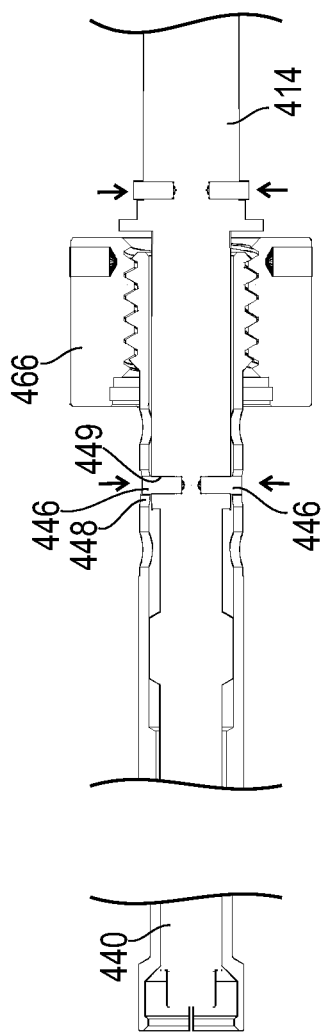
FIG. 67 is a break away cross section view of components shown in FIG. 34.
Figure 68:
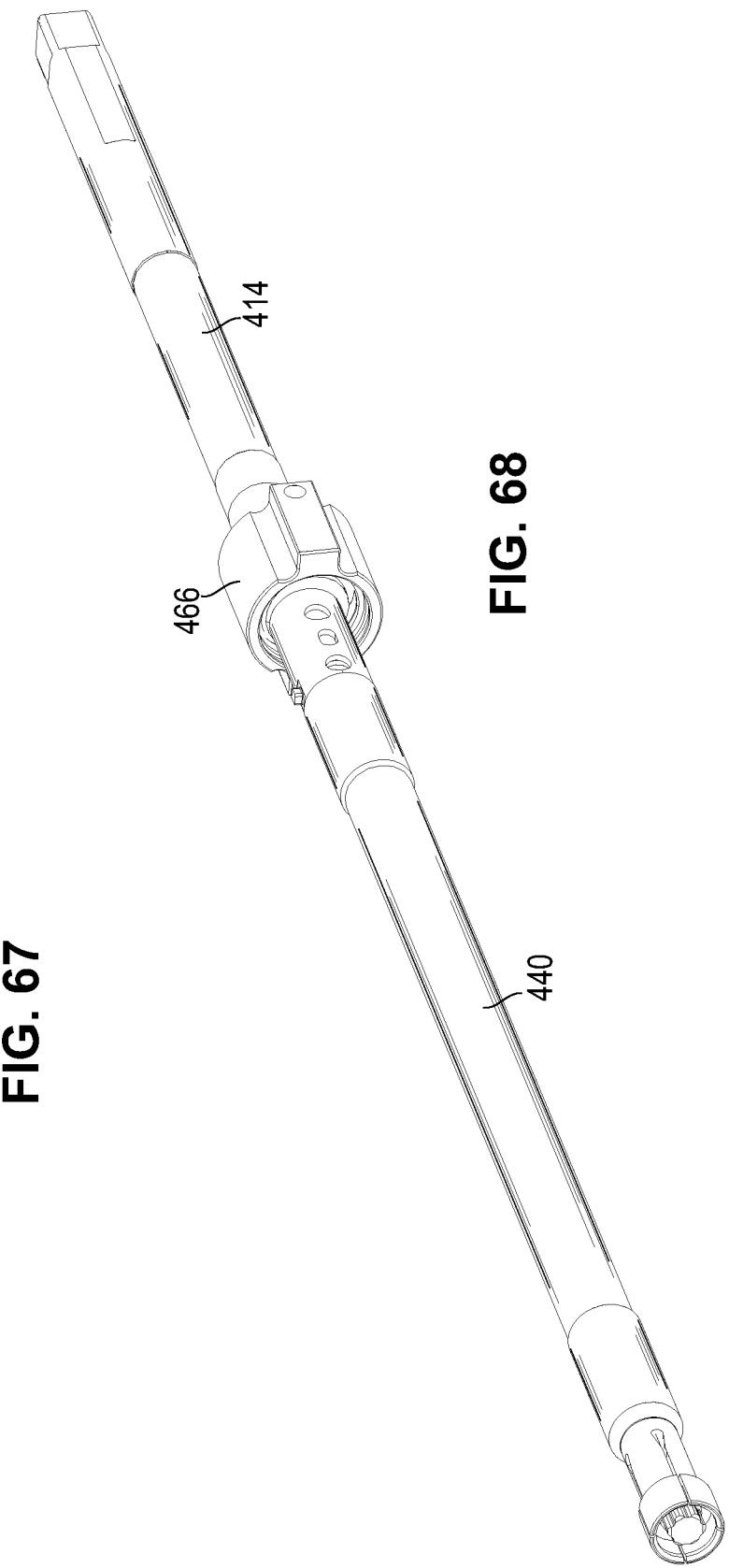
FIG. 68 is a perspective view of components shown in FIG. 34.
Figure 69:
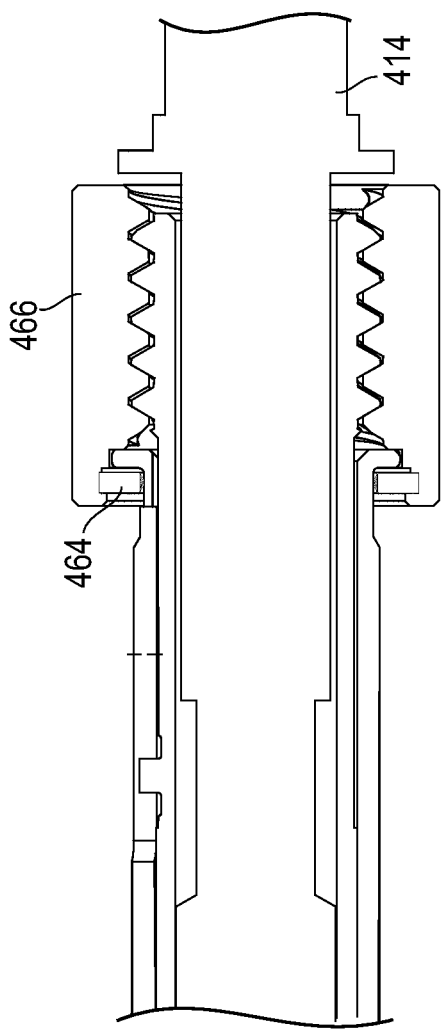
FIG. 69 is a break away cross section view of components shown in FIG. 34.
Figure 70:
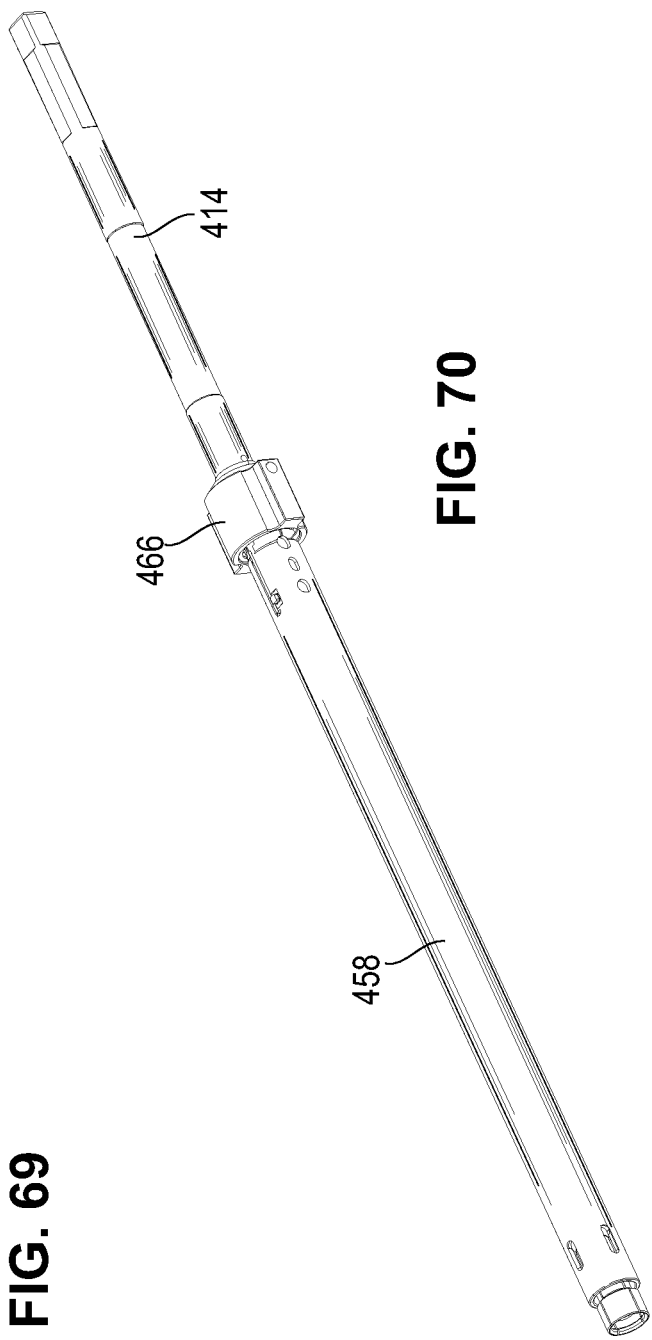
FIG. 70 is a perspective view of components shown in FIG. 34.
Figure 74:
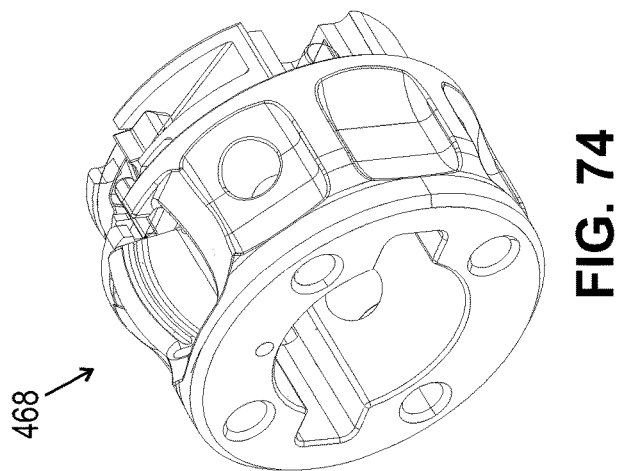
FIG. 74 is a perspective view of components shown in FIG. 71.
Figure 72:
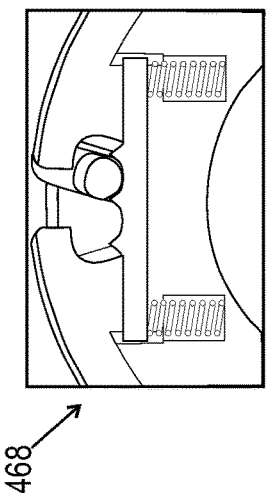
FIG. 72 is a cross section view of components shown in FIG. 71.
Figure 73:
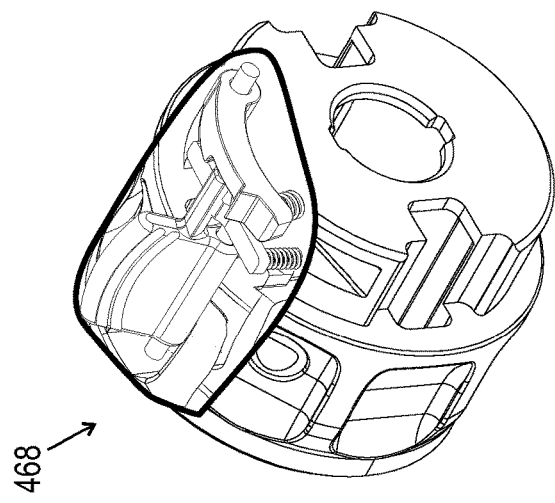
FIG. 73 is a perspective in part cutaway view of components shown in FIG. 71.
Figure 71:
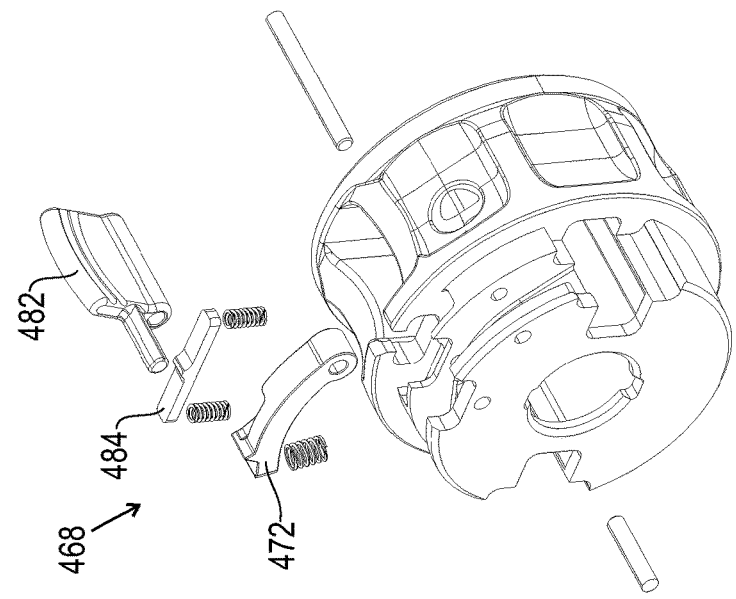
FIG. 71 is a perspective view of components shown in FIG. 34 with parts separated.
Figure 79:
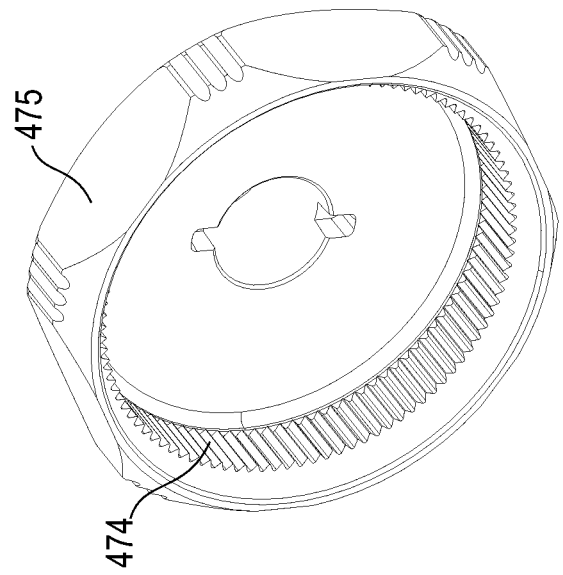
FIG. 79 is a break away view of components shown in FIG. 34.
Figure 78:
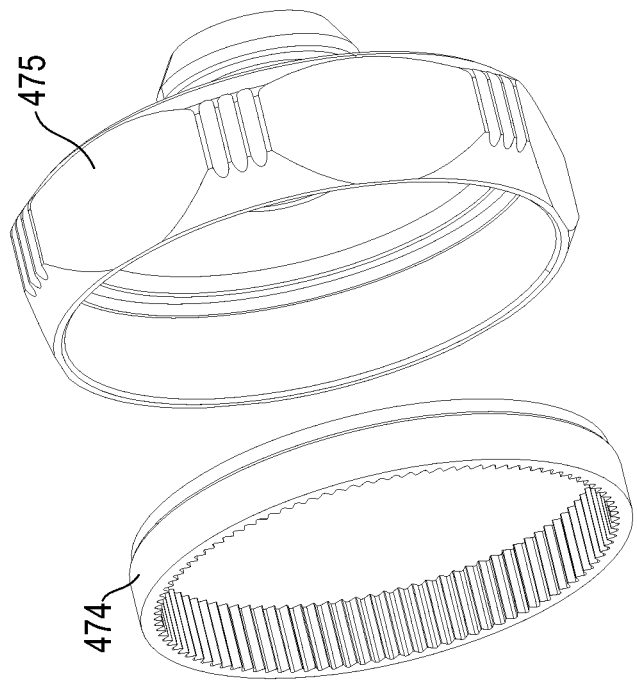
FIG. 78 is a break away view of components shown in FIG. 34.
Figure 80:
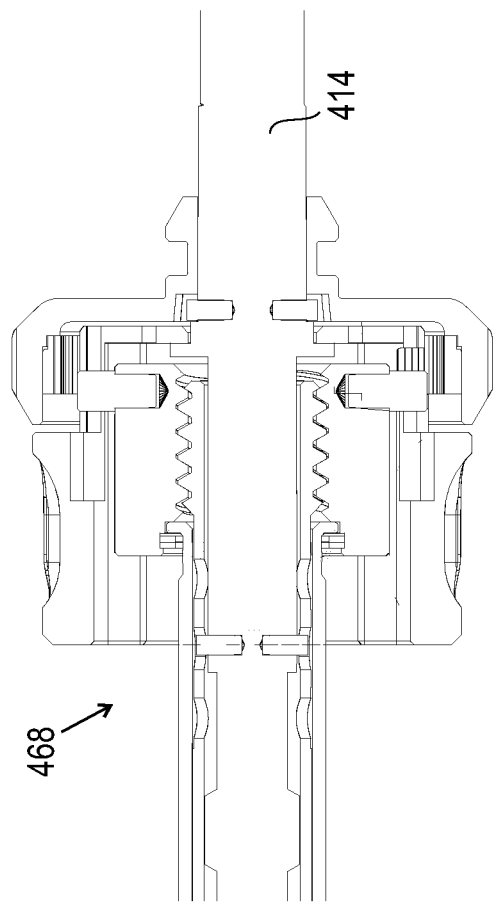
FIG. 80 is a break away cross section view of components shown in FIG. 34.
Figure 81:
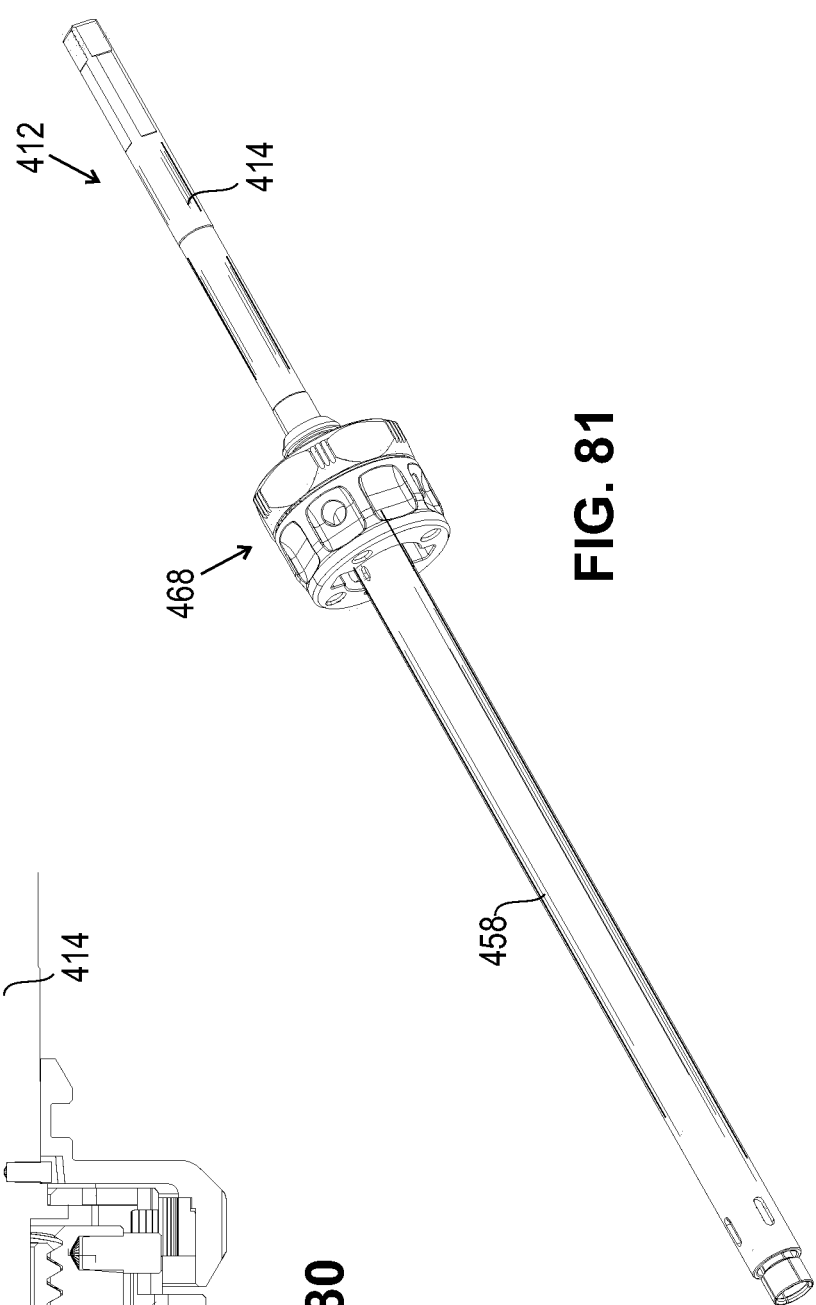
FIG. 81 is a perspective view of components shown in FIG. 34.

To place surgical driver 412 in the non-locked orientation which releases bone fastener 120 from surgical driver 412, lever 482 of lock 480 is translated in a direction, shown by arrow S in FIG. 60 to orient lock 480 in the unlocked position to disengage ratchet 473. Sleeve 458 is translated in a direction, shown by arrow T in FIG. 62 via rotation of knob 470 in the second direction shown by arrow P in FIG. 61. End 462 of sleeve 458 disengages with collet 452 to move into the expandable configuration around head 124 of bone fastener 120 to position surgical driver 412 in the non-locked orientation. In some embodiments, when lock 480 is oriented in the unlocked position, knob 470 freely rotates to translate sleeve 458 relative to sleeve 440 and can place surgical driver 412 in the locked orientation without ratchet 473 engagement. In some embodiments, navigation, as described herein, can be implemented with surgical driver 412.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    a first member defining a longitudinal axis and including a first mating surface engageable with a second mating surface of a fastener;
    a second member including an expandable portion;
    a third member comprising a sleeve engageable with the expandable portion to releasably capture the fastener;
    a first lever connected to the first member;

a compressible member disposed between the first lever and the first member, the compressible member including one or more conical spring washers; and a second lever connected with the first lever via a pivot, the levers being rotatable relative to the longitudinal axis between a non-locked orientation and a locked orientation such that the pivot is rotatable past axial alignment to fix a position of the first member relative to the fastener.

2. A surgical instrument as recited in claim 1, wherein the first lever includes a link having a flange and a shaft, the compressible member being disposed about the shaft.

3. A surgical instrument as recited in claim 1, wherein the conical spring washers include a first plurality of washers oriented in a first axial direction and a second plurality of washers oriented in a second opposite axial direction.

4. A surgical instrument as recited in claim 1, wherein the compressible member is engageable with the first member to tension the first member with a force in a range of 100 through 1000 lbf.

5. A surgical instrument as recited in claim 1, wherein the compressible member is engageable with the first member to tension the first member with a force of 300 lbf.

6. A surgical instrument as recited in claim 1, wherein the compressible member is engageable with the first member to resist and/or prevent movement of the second mating surface relative to the longitudinal axis in a selected variational tolerance in a range of 1 through 5 mm.

7. A surgical instrument as recited in claim 1, in the locked orientation the pivot is rotatable past axial alignment in a selected dimension in a range of 0.25 through 3 mm.

8. A surgical instrument as recited in claim 1, wherein the first lever is engageable to dispose the levers in the locked orientation and the second lever is engageable to release the levers from the locked orientation.

9. A surgical instrument comprising:
a driver defining a longitudinal axis and being engageable with a head of a screw shank;
a first sleeve including a collet;
a second sleeve engageable with the collet to releasably capture the head;
a first link connected to the driver;
a compressible member disposed between the first link and the driver, the compressible member including one or more conical spring washers; and
a second link connected with the first link via a pivot, the links being rotatable relative to the longitudinal axis between a non-locked orientation and a locked orientation such that the pivot is rotatable past axial alignment to fix a position of the driver relative to the head.

10. A surgical instrument as recited in claim 9, wherein the first link includes a shaft, the compressible member being disposed about the shaft.

11. A surgical instrument as recited in claim 9, wherein the conical spring washers include a first plurality of washers oriented in a first axial direction and a second plurality of washers oriented in a second opposite axial direction.

12. A surgical instrument comprising:
a first member defining a longitudinal axis and including a collet engageable with an implant;
a second member comprising a sleeve engageable with the collet to releasably capture the implant;
a first link connected to the first member;
a compressible member disposed between the first link and the first member, the compressible member including one or more conical spring washers; and
a second link connected with the first link via a pivot, the links being rotatable relative to the longitudinal axis between a non-locked orientation and a locked orientation such that the pivot is rotatable past axial alignment to fix a position of the first member relative to the implant.

13. A surgical instrument as recited in claim 12, wherein the first link includes a shaft, the compressible member being disposed about the shaft.

14. A surgical instrument as recited in claim 12, wherein the first link includes a flange and a shaft, the compressible member being disposed about the shaft.

15. A surgical instrument as recited in claim 12, wherein the conical spring washers include a first plurality of washers oriented in a first axial direction and a second plurality of washers oriented in a second opposite axial direction.

16. A surgical instrument as recited in claim 12, wherein the first member is a first sleeve and the second member is a second sleeve.

17. A surgical instrument as recited in claim 12, wherein the first link is engageable to dispose the links in the locked orientation and the second link is engageable to release the links from the locked orientation.

18. A surgical instrument as recited in claim 12, wherein the implant is a screw and the collet is engageable with a head of the screw.

19. A surgical instrument as recited in claim 12, wherein the compressible member is engageable with the first member to tension the first member with a force in a range of 100 through 1000 lbf.

20. A surgical instrument as recited in claim 12, wherein the compressible member is engageable with the first member to tension the first member with a force of 300 lbf.

* * * * *